US011046991B2

(12) United States Patent
Anderson et al.

(10) Patent No.: US 11,046,991 B2
(45) Date of Patent: Jun. 29, 2021

(54) RAPID PRECONCENTRATION OF VIABLE BACTERIA USING MAGNETIC IONIC LIQUID FOR PCR AMPLIFICATION AND CULTURE-BASED DIAGNOSTICS

(71) Applicant: Iowa State University Research Foundation, Inc., Ames, IA (US)

(72) Inventors: Jared L. Anderson, Ames, IA (US); Kevin D. Clark, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 408 days.

(21) Appl. No.: 15/950,916

(22) Filed: Apr. 11, 2018

(65) Prior Publication Data

US 2018/0298417 A1 Oct. 18, 2018

Related U.S. Application Data

(60) Provisional application No. 62/484,620, filed on Apr. 12, 2017.

(51) Int. Cl.
*C12Q 1/04* (2006.01)
*G01N 33/487* (2006.01)
*C12Q 1/24* (2006.01)
*G01N 33/543* (2006.01)
*H01F 1/44* (2006.01)
*H01F 1/42* (2006.01)

(52) U.S. Cl.
CPC .......... *C12Q 1/04* (2013.01); *C12Q 1/24* (2013.01); *G01N 33/48735* (2013.01); *G01N 33/54333* (2013.01); *H01F 1/447* (2013.01); *H01F 1/42* (2013.01)

(58) Field of Classification Search
CPC ...... C12Q 1/04; C12Q 1/24; G01N 33/48735; G01N 33/54333; H01F 1/447; H01F 1/42
See application file for complete search history.

(56) References Cited

U.S. PATENT DOCUMENTS

| 5,158,703 | A | * | 10/1992 | Takuma | C08K 5/0091 |
| | | | | | 252/301.19 |
| 5,916,539 | A | * | 6/1999 | Pilgrimm | A61K 49/186 |
| | | | | | 424/9.322 |
| 6,203,725 | B1 | * | 3/2001 | Ogiso | C09K 11/06 |
| | | | | | 252/301.35 |
| 10,280,416 | B1 | * | 5/2019 | Anderson | C07F 15/025 |
| 2016/0002269 | A1 | * | 1/2016 | Shanzer | C07F 5/003 |
| | | | | | 435/6.1 |
| 2020/0325525 | A1 | * | 10/2020 | Anderson | C12Q 1/04 |

OTHER PUBLICATIONS

B. Monteiro et al., 53 Chemical Communications, 850-853 (2017) (Year: 2017).*
CAS Abstract of B. Monteiro et al., 53 Chemical Communications, 850-853 (2017) (Year: 2017).*
T Shepherd et al., 212 Nature (London, United Kingdom), 745 (1966) (Year: 1966).*
CAS Abstract of T Shepherd et al., 212 Nature (London, United Kingdom), 745 (1966) (Year: 1966).*
CAS Abstract of H. Matschiner et al., 260 Zeitschrift fuer Physikalische Chemie (Leipzig), 538-544 (1979) (Year: 1979).*
CAS Abstract of H. Mezyketal., 11 Physical Chemistry Chemical Physics, 10152-10156 (2009) (Year: 2009).*
H. Mezyk et al., 11 Physical Chemistry Chemical Physics, 10152-10156 (2009) (Year: 2009).*
CAS Abstract of P. Zhang et al., 48 Chemical Communications, 2334-2336 (2012) (Year: 2012).*
P. Zhang et al., 48 Chemical Communications, 2334-2336 (2012) (Year: 2012).*
María J. Trujillo-Rodríguez et al. 172 Talanta, 86-94 (2017) (Year: 2017).*
H. Matschiner et al., 260 Zeitschrift fuer Physikalische Chemie (Leipzig), 538-544 (1979) (Year: 1979).*
CAS Abstract and Indexed Compounds, C. Pereira et al., 91 Polyhedron, 42-46 (2015) (Year: 2015).*
C. Pereira et al., 91 Polyhedron, 42-46 (2015) (Year: 2015).*
S. Pierson et al., 41 New Journal of Chemistry, 5498-5505 (2017) (Year: 2017).*
K. Clark et al., 56 Angew. Chem. Int. Ed., 7630-7633 (2017) (Year: 2017).*
K. Clark et al., 409 Anal Bioanal Chem, 4983-4991 (2017) (Year: 2017).*
A. Chisvert et al., 983 Analytica Chimica Acta, 130-140 (2017) (Year: 2017).*
Chapman, P.A. et al., "Comparison of Culture, PCR and Immunoassays for Detecting *Escherichia coli* O157 Following Enrichment Culture and Immunomagnetic Separation Performed on Naturally Contaimined Raw Meat Products", International Journal of food Microbiology 68, pp. 11-20. Jan. 6, 2001.
Clark, Kevin D. et al., "Magnetic Ionic Liquids in Analytical Chemistry: A Review", Analytica Chimica Acta 934, pp. 9-21. Jun. 13, 2016.
Clark, Kevin D. et al., "Extraction of DNA by Magnetic Ionic Liquids: Tunable Solvents for Rapid and Selective DNA Analysis", Analytical Chemistry, 87, pp. 1552-1559. Jan. 11, 2015.

(Continued)

*Primary Examiner* — Alexander R Pagano
(74) *Attorney, Agent, or Firm* — McKee, Voorhees & Sease, PLC

(57) ABSTRACT

In this disclosure, transition and rare earth metal-based magnetic ionic liquids (MILs) are successfully prepared in a two-step synthesis and used to extract viable bacteria from a liquid sample. The disclosed MILs are extremely hydrophobic MILs and were insoluble in aqueous solution at 0.01% (v/v). Furthermore, these MILs were miscible in a variety of polar and non-polar organic solvents. Moreover, these MILs possess low viscosity and increased magnetic susceptibility. These MILs possess unique characteristics that can have great potential uses in various chemical applications such as extraction solvents in LLE, liquid electrochromic materials (Co-based MILs), and novel reaction media for organic synthesis.

31 Claims, 16 Drawing Sheets
(3 of 16 Drawing Sheet(s) Filed in Color)

(56) References Cited

OTHER PUBLICATIONS

Clark, Kevin D. et al., "Magnetic Ionic Liquids as PCR-Compatible Solvents for DNA Extraction from Biological Samples", Chem. Commun., 51, pp. 16771-16773. Sep. 27, 2015.

Clark, Kevin D. et al., "Preservation of DNA in Nuclease-rich Samples Using Magnetic Ionic Liquids", The Royal Society of Chemistry, pp. 39846-39851. Apr. 11, 2016.

Heininger, Alexandra, et al., "PCR and Blood Culture for Detection of *Escherichia coli* Bacteremia in Rats", Journal of Clinical Microbiology, pp. 2479-2482. Apr. 20, 1999.

Mehdi, Hasan et al., "Hydrophobic Ionic Liquids with Strongly Coordinating Anions", The Royal Society of Chemistry, 46, pp. 234-236. Nov. 21, 2009.

Nacham, Omprakash et al., "Synthesis and Characterization of the Physicochemical and Magnetic Properties for Perfluoroalkyl Ester and Fe(III) Carboxylate-based Hydrophobic Magnetic Ionic Liquids", The Royal Society of Chemistry, 5, pp. 11109-11117. Jan. 13, 2016.

Nacham, Omprakash et al., "Synthetic Strategies for Tailoring the Physicochemical and Magnetic Properties of Hydrophobic Magnetic Ionic Liquids", Chemistry of Materials, 27, pp. 923-931. Jan. 5, 2015.

Pêrez, Fidel G. et al., "Immunomagnetic Separation with Mediated Flow Injection Analysis Amperometric Detection of Viable *Escherichia coli* O157", Analytical Chemistry, vol. 70, No. 11, pp. 2380-2386. Jun. 1, 1998.

Rosatella, Andreia A., et al., "New Low Viscous Cholinium-based Magnetic Ionic Liquids", New J. Chem., 40, pp. 3124-3129. Jan. 18, 2016.

Sheridan, G.E.C. et al., "Detection of mRNA by Reverse Transcription-PCR as an Indicator of Viability in *Escherichia coli* Cells", Applied and Environmental Microbiology, pp. 1313-1318. Jan. 26, 1998.

Xie, Zai-Lai et al., "Thermomorphic Behavior of the Ionic Liquids", Chem Phys Chem., 12, pp. 364-368. 2011.

Yoshida, Yukihiro et al., "Influence of Structural Variations in 1-alkyl-3-methylimidazolium Cation and Tetrahalogenoferrate(III) Anion on the Physical Properties of the Paramagnetic Ionic Liquids", J. Mater Chem., 16, pp. 1254-1262. Jan. 9, 2006.

Zhang, Suojiang et al., "ChemComm", Ionic Liquids, Journal Homepage pp. 1-4. Dec. 14, 2011.

\* cited by examiner

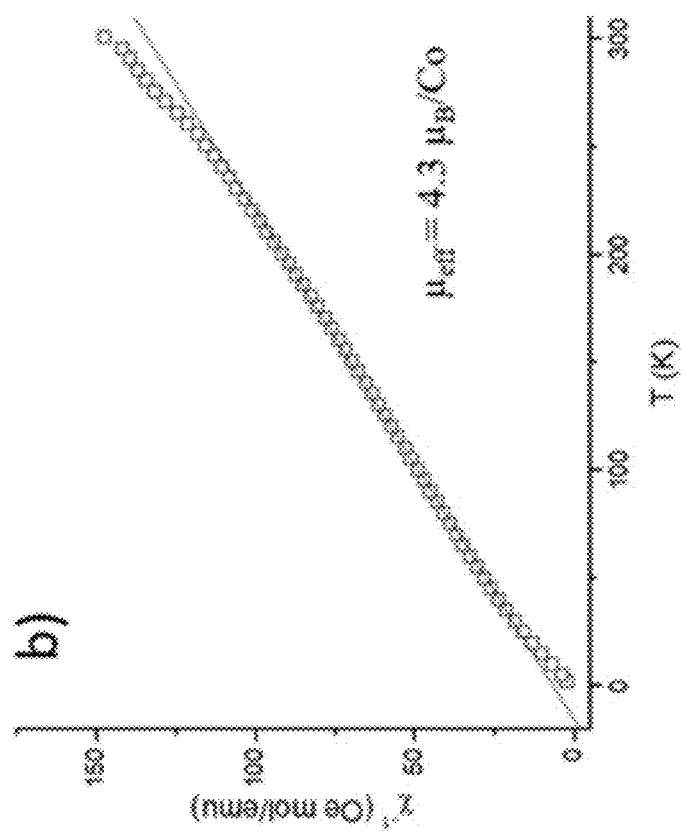
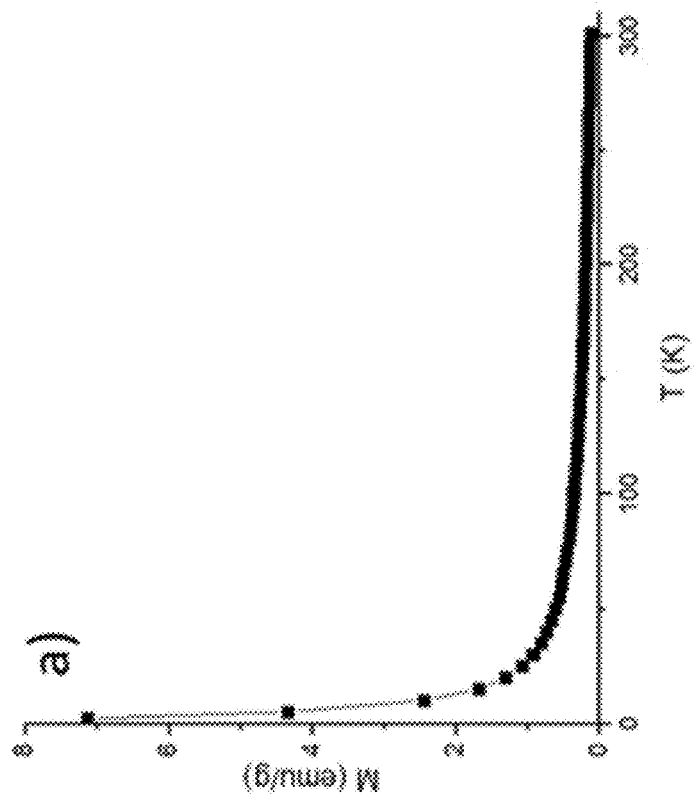
FIG. 4A
FIG. 4B

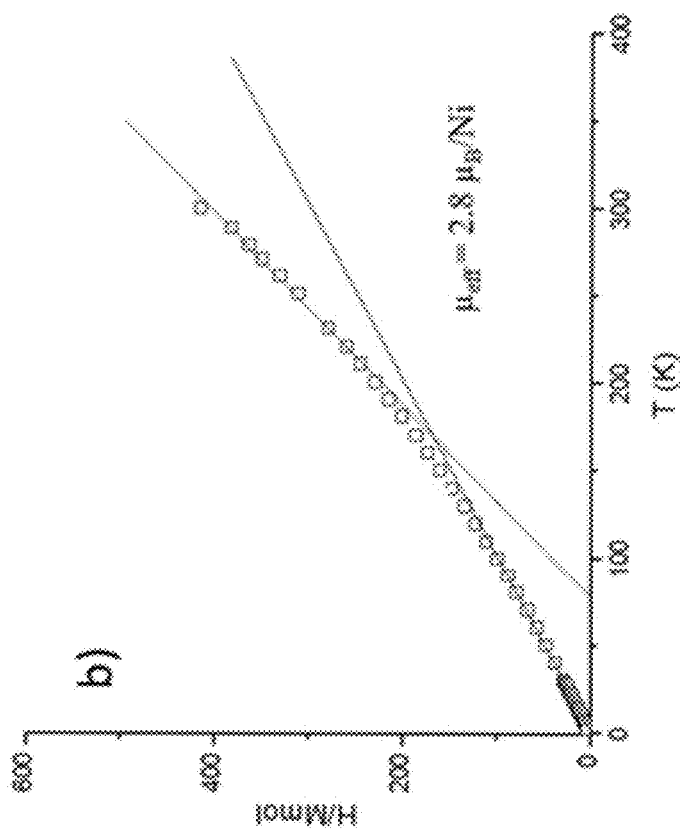
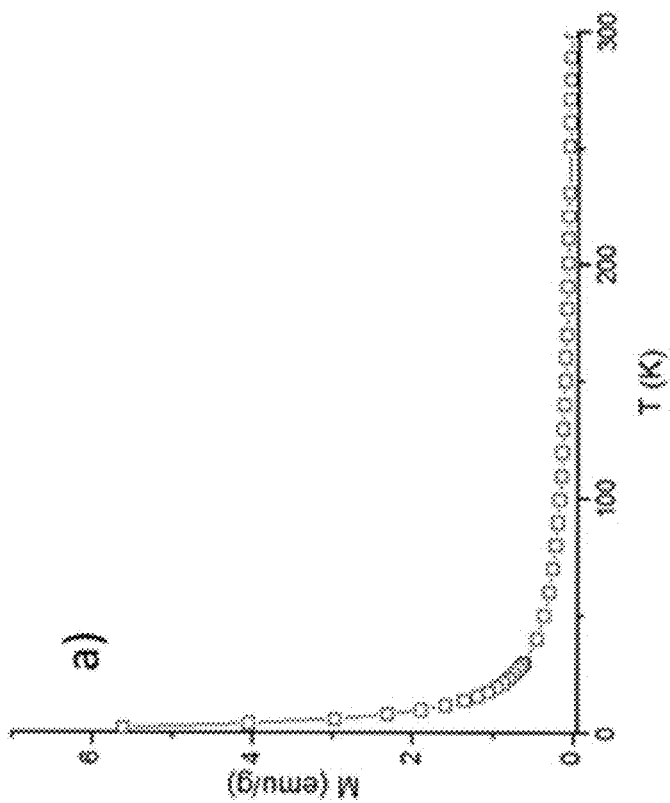
FIG. 6B
FIG. 6A

RAPID PRECONCENTRATION OF VIABLE BACTERIA USING MAGNETIC IONIC LIQUID FOR PCR AMPLIFICATION AND CULTURE-BASED DIAGNOSTICS

CROSS-REFERENCE TO RELATED APPLICATIONS

This application claims priority under 35 U.S.C. § 119 to provisional application U.S. Ser. No. 62/484,620, filed Apr. 12, 2017, herein incorporated by reference in its entirety. The entire contents of this patent application are hereby expressly incorporated herein by reference including, without limitation, the specification, claims, and abstract, as well as any figures, tables, or drawings thereof.

GRANT REFERENCE

This invention was made with government support under Grant number CHE-1602091 awarded by the National Science Foundation. The government has certain rights in the invention.

FIELD OF THE INVENTION

The present disclosure is related to a new class of magnetic ionic liquids (MILs), a novel method for their synthesis, and a method to use these MILs for extraction and preconcentration of bacteria from liquid samples. Specifically, hydrophobic magnetic ionic liquids (MILs) comprising a paramagnetic anionic component containing a transition or rare earth metal ion and hydrophobic chelating agent and a hydrophobic cationic component and their two-step synthesis method are disclosed. These disclosed MILs possess a low viscosity, thermal stability, and low water solubility, and therefore can be used in a wide range of applications. Especially, these MILs can be used to extract or concentrate bacteria from aqueous samples and to enable faster and more sensitive live bacteria detection and quantification, especially when some MILs can keep extracted bacteria viable.

BACKGROUND OF THE INVENTION

Ionic liquids (ILs) have garnered much attention in the last decade due to an array of attractive physicochemical properties including negligible vapor pressure, high thermal stability, high conductivity, and tunable miscibility with water and organic solvents. These fascinating compounds are generally comprised of an organic cation paired with an organic/inorganic anion and possess melting points at or below 100° C. The physicochemical properties of ILs can be altered and tuned through the careful manipulation of cation/anion pairing making them highly versatile materials.

Magnetic ionic liquids (MILs) are a subclass of ILs that share many of the advantageous physicochemical properties of traditional ILs. MILs possess a paramagnetic metal center within the cation and/or anion that allow them to be modulated by an external magnetic field. The 1-butyl-3-methylimidazolium tetrachloroferrate(III) ([BMIM$^+$][FeCl$_4^-$]) MIL was the first example of an IL that incorporated a paramagnetic center in its chemical structure. Since then, a variety of transition and rare earth metals, such as Co(II), Mn(II), Fe(III), Dy(III), Gd(III), Ho(III), and Nd(III), have been used as paramagnetic centers in the preparation of MILs (K. D. Clark, O. Nacham, J. A. Purslow, S. A. Pierson and J. L. Anderson, *Anal. Chim. Acta,* 2016, 934, 9-21).

MILs have enjoyed increasing popularity in applications such as liquid-liquid extractions (LLE), liquid-liquid microextractions (LLME), stationary phases for comprehensive two-dimensional gas chromatography (GC×GC), electrochemical applications, and catalysis. The promising field of MILs is expanding rapidly, and thus the need for more robust, hydrophobic MILs has never been greater.

Applications that utilize MILs as extraction solvents from aqueous environments require MILs that are extremely hydrophobic and chemically stable to retain its magnetic susceptibility and not suffer from dissolution or loss of the solvent. Importantly, the magnetic susceptibility of MILs can only be exploited if they possess very little solubility in the solvent to which they are added (e.g., water). MILs that are room temperature liquids are required for applications performed at ambient temperatures. Therefore, MILs possessing high hydrophobicity, low melting points, low viscosity, as well as high magnetic susceptibility are all favorable properties when they are utilized as solvent systems in many applications (e.g., extractions and catalytic solvents).

Additionally, there is an underlying issue in MIL design that relates to the chemical stability of the MIL in an aqueous environment. Although it is a popular choice for the anion component of MILs, the [FeCl$_4^-$] anion has been shown to undergo hydrolysis in water thereby influencing solution pH and limiting the amount of MIL that can be recovered in applications involving water (Z. L. Xie and A. Taubert, *ChemPhyschem,* 2011, 12, 364-368). A design challenge revolves around creating MILs that encompass all of the aforementioned features with minimal compromise of any single feature.

The incorporation of hydrophobic trihexyl(tetradecyl)phosphonium ([P$_{66614}^+$]) and Aliquat 336 cations has been a well-utilized strategy for creating hydrophobic ILs. Furthermore, the weakly coordinating bis[(trifluoromethyl)sulfonyl]imide [NTf$_2^-$] anion has been used to increase the hydrophobicity as well as lower the viscosity for many classes of ILs. However, MILs with [NTf$_2^-$] anions require either a multi-cationic platform with heteroanions or a paramagnetic component in the cation of the MIL to establish paramagnetic susceptibility. MILs utilizing the [NTf$_2^-$] anion in di- or tricationic frameworks involve tedious multistep synthetic pathways while some MILs with paramagnetic cations have been shown to exhibit poor stability under ambient conditions (O. Nacham, K. D. Clark, H. Yu and J. L. Anderson, *Chem. Mater.,* 2015, 27, 923-931; Y. Yoshida and G. Saito, *J. Mater. Chem.,* 2006, 16, 1254; O. Nacham, K. D. Clark and J. L. Anderson, *RSC Adv.,* 2016, 6, 11109-11117). Thus, it is the objective of this disclosure to improve the hydrophobicity, viscosity, and synthesis of MILs to circumvent the challenges that were encountered by the prior art MILs.

Determining the amount and type of bacteria in food, water supplies, clinical samples, and environment at large is essential for preserving and improving public health. Without proper and sensitive identification and quantification measurements, exposure to pathogenic bacteria may lead to negative health outcomes that include infections, gastrointestinal illness, and/or renal failure, particularly for individuals with compromised immune systems. To keep people safe, food, water, clinical, and environmental samples need to be tested.

Bacterium detection methods based on cell cultures, biosensors, and nucleic acid-based diagnostics (e.g., PCR) are sensitive, but are susceptible to false negative/false positive results when large quantities of background flora or chemical interferences are insufficiently removed from the sample.

Furthermore, sample heterogeneity due to non-uniform distribution of bacteria, high viscosity, and/or suspended solids in the sample may influence assay detection limits and reproducibility. One way to overcome such susceptibility is to isolate and preconcentrate target bacteria prior to analysis.

Enrichment cultures are the most common and least expensive techniques for the preconcentration of viable bacteria. In these approaches, samples are incubated within a selective liquid cultivation medium to enrich target bacteria and suppress the growth of endogenous or contaminating microorganisms.

However, for the culture-based enrichment methods employed for the analysis of microorganisms in food, environmental, and clinical samples, incubation times may range from several hours to several days depending on the microorganism, resulting in limited sample throughput. Moreover, some bacteria are uncultured or cannot be cultured in a laboratory setting and present considerable challenges when the detection of bacteria at low concentration is required. In addition, some pathogens can cause illness at extremely low concentrations, regulatory agencies may impose low or even "zero tolerance" policies for viable bacteria in water or food products. Clearly, there is a continuous need for faster and more sensitive techniques for unambiguous pathogen identification and quantification in general and for more effective preconcentration of viable bacteria in particular.

Contemporary sample preparation methods for the analysis of bacteria aim to increase sample throughput, specificity, and assay detection limits. Magnetic separation approaches exploit the magnetic behavior of a sorbent material and are frequently employed for the rapid and efficient enrichment of bacteria (Perez FG, Mascini M, Tothill IE, Turner AP. Immunomagnetic separation with mediated flow injection analysis amperometric detection of viable *Escherichia coli* O157, *Anal. Chem.* 1998; 70:2380-6).

In these methods, a magnetoactive substrate is dispersed in a sample solution to extract small quantities of target bacteria and subsequently isolated by applying a magnetic field. Functionalized magnetic particles that utilize affinity or immunoaffinity capture have been shown to enhance the selectivity for target microorganisms while significantly decreasing the overall analysis time. Unfortunately, immunoaffinity approaches require antibodies for pathogen capture that often exhibit poor stability under harsh sample conditions and are susceptible to denaturation. Furthermore, these techniques require complicated substrate immobilization procedures to functionalize the magnetic support and are cost-prohibitive for most users.

Magnetic ionic liquids (MILs) are a class of compounds that have recently emerged as solvents for bioanalytical applications. By incorporating one or more paramagnetic components into the cation/anion moiety, MILs exhibit susceptibility to an applied magnetic field. While conventional ionic liquids (ILs) and IL-based sorbents have been successfully applied for the extraction of pathogens from food samples and aqueous samples, the paramagnetic nature of MILs represents a significant advantage over non-magnetic ILs and is ideal for magnet-based platforms that can be readily automated to greatly increase sample throughput. Carefully designing their chemical structures in a similar way as applied to ILs, one can control the physicochemical properties of MILs.

Such approach has resulted in magnetoactive solvents with reduced cytotoxicity (Rosatella A A, Siopa F, Frade R F M, Afonso C A M. New low viscous cholinium-based magnetic ionic liquids. *New J. Chem.* 2016), hydrophobicity (Nacham O, Clark K D, Yu H, Anderson J L. Synthetic strategies for tailoring the physicochemical and magnetic properties of hydrophobic magnetic ionic liquids. *Chem. Mater.* 2015; 27:923-31), and biomolecule extraction/preservation capabilities (Clark K D, Nacham O, Yu H, Li T, Yamsek M M, Ronning D R, Anderson J L. Extraction of DNA by magnetic ionic liquids: tunable solvents for rapid and selective DNA analysis. Anal. Chem. 2015; 87:1552-9 and Clark K D, Sorensen M, Nacham O, Anderson J L. Preservation of DNA in nuclease-rich samples using magnetic ionic liquids, RSC Adv. 2016; 6:39846-51). Very recently, tetrahaloferrate(III)-based MILs were applied in a DNA extraction method that was directly interfaced with PCR amplification for the rapid detection of bacterial plasmid DNA in crude cell lysate (Clark K D, Yamsek M M, Nacham O, Anderson J L. Magnetic ionic liquids as PCR-compatible solvents for DNA extraction from biological samples. Chem. Commun. 2015; 51:16771-73).

Although diagnostic PCR assays are extremely valuable for many applications, the detection of viable bacteria in a sample is an important requirement for pathogen analysis. Thus, to use MILs or MIL-based sorbents for the extraction of pathogens from a sample, MILs for extracting or preconcentrating viable pathogen is still needed.

Accordingly, it is an objective of the present disclosure to provide a series of magnetic ionic liquids (MILs) for the extraction and preconcentration of viable bacteria from aqueous samples. It is also an objective of the present disclosure to provide a method for utilizing the claimed MILs for identification and quantification of a certain type of pathogens from a sample.

BRIEF SUMMARY OF THE INVENTION

In one aspect, disclosed herein is a magnetic ionic liquid, comprising a paramagnetic anionic component and a cationic component, wherein the cationic component has a general formula (I)

$$[(PR^1R^2R^3R^4)^+] \tag{I}$$

wherein $R^1$, $R^2$, $R^3$, and $R^4$ are independently an unsubstituted or substituted alkyl; the paramagnetic anionic component has the following general formula (II), $$[M(Y)_x^-] \tag{II}$$

wherein M is transition metal or rare earth metal ion; and Y is a chelating agent having the general formula (III),

$R^{10}$ and $R^{11}$ are independently a substituted or unsubstituted methyl, phenyl, thiophenyl, napthyl, alkyl, or aryl group; and x is 3 or 4.

In another aspect, disclosed herein is an improved method to synthesize a magnetic ionic liquid. The disclosed method comprises mixing ammonium hydroxide, an alcohol, a chelating agent, and metal chloride salt in a reaction vessel for the period of a reaction time at a reaction temperature to produce a corresponding chelated metal anionic component; and mixing a cationic component and the anionic component to produce a magnetic ionic liquid, wherein the metal salt is paramagnetic transition or rare earth metal salt; the anionic component has the general formula, $[M(Y)_x^-]$, wherein M is transition metal or rare earth metal ion; and the chelating agent comprising a negative ion, Y having the general formula (III),

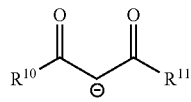
(III)

$R^{10}$ and $R^{11}$ are independently a substituted or unsubstituted methyl, phenyl, thiophenyl, napthyl, alkyl or aryl group; and x is 3 or 4; the cationic component is $[(PR^1R^2R^3R^4)^+]$, wherein $R^1$, $R^2$, $R^3$, and $R^4$ are independently an unsubstituted alkyl; the vessel is capped and the chelating agent is added slowly to the vessel containing the alcohol and ammonia hydroxide before the metal salt is added to the vessel.

In yet another aspect, disclosed herein is a method of extracting, detecting, identifying, quantifying, or a combination thereof a viable bacterium from a sample, the method comprises contacting a sample with a magnetic ionic liquid for the period of a contact time, wherein the sample comprises a viable bacterium; and the magnetic ionic liquid extracts the bacterium from the sample.

The magnetic ionic liquids disclosed herein are hydrophobic and insoluble in aqueous solution at 0.01% (v/v), yet are miscible in a variety of polar and non-polar organic solvents. Furthermore, the magnetic ionic liquids disclosed herein exhibited low viscosities, thermal stability, and solution stability, and therefore can be handled easily and have great potential uses in various chemical applications such as extraction solvents in liquid-liquid extraction (LLE), liquid electrochromic materials (Co-based MILs), and novel reaction media for organic synthesis. In addition, the magnetic ionic liquids disclosed herein can extract a viable bacterium from a sample. Some of the MILs disclosed here can keep the bacterium viable after the extraction or preconcentration. Thus, one can extract a viable bacterium from a sample, using the magnetic ionic liquids disclosed herein, so the bacterium can be detected, quantified, or both with improved accuracy, lower detection limit, and within a shorter period of time.

The disclosed method to synthesize the disclosed magnetic ionic liquid is a simple two-step synthesis. This synthesis method is more efficient and of higher yield.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing or photograph executed in color. Copies of this patent or patent application publication with color drawing(s) will be provided by the Office upon request and payment of the necessary fee.

FIG. 4a shows the magnetization of the $[P_{66614}^+][Co(hfacac)_3^-]$ MIL measured as a function of temperature in a 20000 Oe applied magnetic field.

FIG. 4b shows the Curie-Weiss fit of the linear portion of the reciprocal susceptibility for the $[P_{66614}+][Co(hfacac)_3^-]$ MIL.

FIG. 6a shows magnetization of the $[P_{66614}^+][Ni(hfacac)_3^-]$ MIL measured as a function of temperature in a 20000 Oe applied magnetic field.

FIG. 6b shows the Curie-Weiss fits of the linear regions of the reciprocal susceptibility above and below the ~150 K anomaly for the $[P_{66614}^+][Ni(hfacac)_3^-]$ MIL.

DETAILED DESCRIPTION OF THE PREFERRED EMBODIMENT

Figure 1:
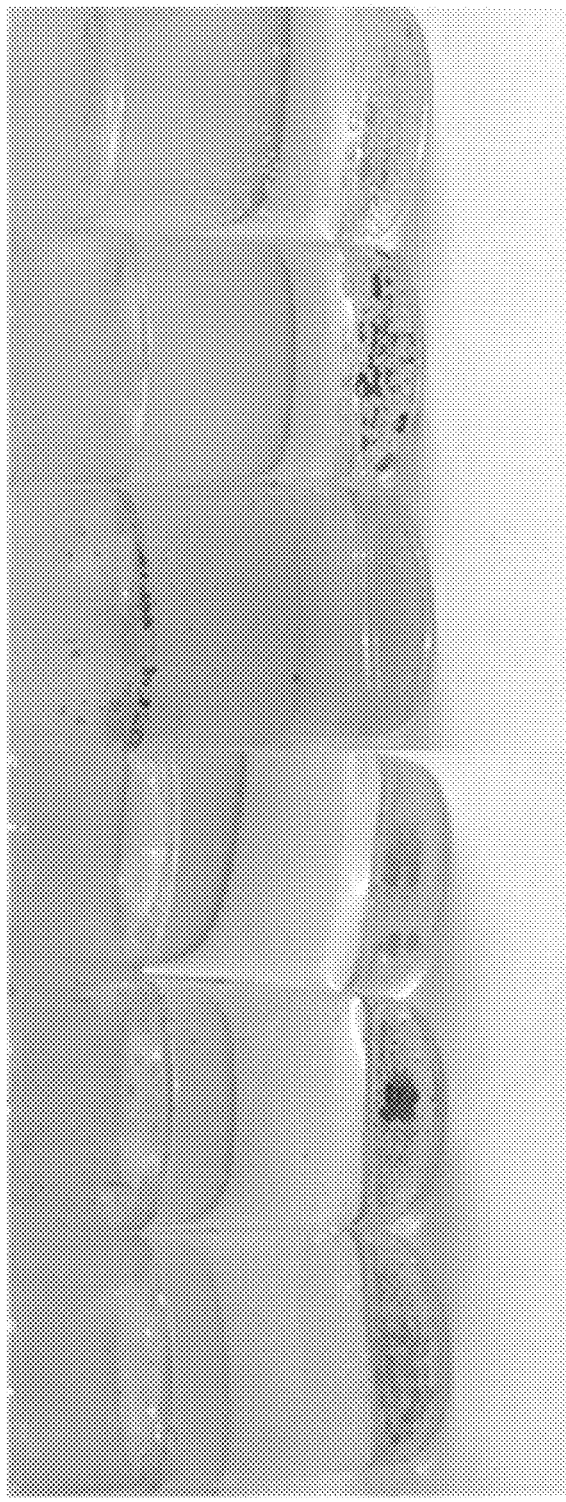
FIG. 1 shows $[P_{66614}^+][FeCl_4^-]$ (left), $[P_{66614}^+][Co(hfacac)_3^-]$ (middle), and $[P_{66614}^+][Nd(hfacac)_4^-]$ (right) before and after heating for 10 minutes at 85° C.

To circumvent the challenges for using the prior art MILs and produce hydrophobic MILs with low viscosity, a new class of MILs is obtained by pairing a hydrophobic cation with a weakly coordinating but also hydrophobic anion that can chelate with paramagnetic metal centers.

In this disclosure, a two-step synthesis is disclosed to create low melting, room temperature transition and rare earth metal-based MILs. Transition metals, such as Co(II), Mn(II), and Ni(II) were incorporated into the MIL structure to create trihexyl(tetradecyl)phosphonium tris(hexafluoroacetylaceto)cobaltate(II) ($[P_{66614}^+][Co(hfacac)_3^-]$), $[P_{66614}^+]$ tris(hexafluoroacetylaceto)manganate(II) ($[Mn(hfacac)_3^-]$), $[P_{66614}^+]$ tris(hexafluoroacetylaceto)nickelate(II) ($[Ni(hfacac)_3^-]$) MILs. Three exemplary rare earth metal centers, dysprosium(III), gadolinium(III) and neodymium (III), were also used to prepare $[P_{66614}^+]$ tetrakis(hexafluoroacetylaceto)dysprosate(III) ($[Dy(hfacac)_4^-]$), $[P_{66614}^+]$ tetrakis(hexafluoroacetylaceto)gadolinate(III) ($[Gd(hfacac)_4^-]$), and $[P_{66614}^+]$ tetrakis(hexafluoroacetylaceto)neodymate(III) ($[Nd(hfacac)_4^-]$) MILs.

It was observed that all of the exemplary MILs disclosed herein have a water solubility of less than 0.01% (v/v), making them ideal for MIL-based applications in aqueous systems. Furthermore, these MILs are found to be soluble in nearly 15 organic solvents. Viscosities of the synthesized MILs ranged from 276.5 centipoise (cP) to 927.9 cP at 23.7° C., making them among the least viscous hydrophobic MILs ever reported. Thermal properties of these exemplary MILs were investigated by monitoring the onset of volatilization/decomposition using flame ionization detection with thermal stabilities ranging from 130-225° C. and suitable for a wide range of applications. In addition, incorporation of Gd(III) and Dy(III) metal centers produced MILs with magnetic moments ($\mu_{eff}$) of 7.7 and 9.7 Bohr magnetons ($\mu_B$), respectively, as determined by superconducting quantum interference device (SQUID) magnetometry. This new class of MILs possess high hydrophobicity, low melting points, low viscosity, and high magnetic susceptibility making them ideal solvents for many applications ranging from catalysis to microfluidic applications where the MIL can be readily controlled and manipulated within the device.

The present disclosure relates to a new class of MILs comprising a transition or rare earth metal complex hydrophobic anion and a hydrophobic cation that can chelate with paramagnetic metal centers, a method to synthesize the disclosed MILs, and a method to use the disclosed MILs to extract a viable bacterium from a sample. The embodiments of the disclosed MILs, synthesis thereof, or methods thereof are not limited to any particular metal ion, chelating species, synthesis method, bacterium, or extraction method which can vary and are understood by skilled artisans based on the present disclosure. It is further to be understood that all terminology used herein is for describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of the disclosed MILs, synthesis thereof, and methods are presented in a range format. The description in range format is merely for convenience and brevity and should not be construed as an inflexible limitation on the scope of the disclosed MILs and methods. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosed MILs and methods pertain. Many methods and materials similar, modified, or equivalent to those described herein can be used in the practice of the embodiments of the disclosed MILs and methods without undue experimentation. The preferred materials and methods are described herein. In describing and claiming the embodiments of the disclosed MILs and methods, the following terminology will be used in accordance with the definitions set out below.

The term "about," as used herein, refers to variations in size, distance or any other types of measurements that can be resulted from the inherent heterogeneous nature of the measured objects and imprecise nature of the measurements themselves. The term "about" also encompasses variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods, and the like. The term "about" also encompasses amounts that differ due to different equilibrium conditions for a composition resulting from a particular initial mixture. Whether or not modified by the term "about", the claims include equivalents to the quantities.

The term "independently" means that where more than one substituent is selected from a number of possible substituents, those substituents may be the same or different.

As used herein, "substituted" refers to an organic group as defined below (i.e., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having 2 to about 30 carbon atoms, and further including at least one double bond. In some embodiments, alkenyl groups have from 2 to about 20 carbon, or typically, from 2 to 10 carbon atoms. Alkenyl groups may be substituted or unsubstituted. Alkenyl groups may be substituted similarly to alkyl groups.

As used herein, the terms "alkylene", cycloalkylene", alkynylene, and alkenylene", alone or as part of another substituent, refer to a divalent radical derived from an alkyl, cycloalkyl, or alkenyl group, respectively, as exemplified by —CH$_2$CH$_2$CH$_2$—. For alkylene, cycloalkylene, alkynylene, and alkenylene groups, no orientation of the linking group is implied.

As used herein, "aryl" or "aromatic" groups are cyclic aromatic hydrocarbons that do not contain heteroatoms. Aryl groups include monocyclic, bicyclic, and polycyclic ring systems. Thus, aryl groups include, but are not limited to, phenyl, azulenyl, heptalenyl, biphenylenyl, indacenyl, florenyl, phenanthrenyl, triphenylenyl, pyrenyl, naphthacenyl, chrysenyl, biphenyl, anthracenyl, indenyl, indanyl, pentalenyl, and naphthyl groups. In some embodimets, aryl groups contain 6-14 carbons, in others from 6 to 12 or 6-10 carbon atoms in the ring portions of the groups. The phrase "aryl groups" includes groups containing fused rings, such as fused aromatic-aliphatic ring systems. Aryl groups may be substituted or unsubstituted.

In one aspect, the present disclosure relates to a magnetic ionic liquid, the magnetic ionic liquid comprises a paramagnetic anionic component and a cationic component, wherein the cationic component has a general formula (I)

[(PR$^1$R$^2$R$^3$R$^4$)$^+$]  (I)

wherein each of R$^1$, R$^2$, R$^3$, and R$^4$ is independently an unsubstituted or substituted alkyl; the paramagnetic anionic component has the following general formula (II),

[M(Y)$_x$$^-$]  (II)

wherein M is transition metal or rare earth metal ion; and Y is a chelating agent having the general formula (III),

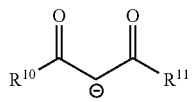

(III)

each of R$^{10}$ and R$^{11}$ is independently a substituted or unsubstituted methyl, phenyl, thiophenyl, napthyl, alkyl, or aryl group; and x is 3 or 4.

In some embodiments, in the magnetic ionic liquid disclosed herein, M is a transition metal ion. In some other embodiments, M is Co, Mn, Ni, or combination thereof.

In some embodiments, in the magnetic ionic liquid disclosed herein, M is a rare earth metal ion. In some other embodiments, M is Dy, Nd, Gd, or a combination thereof. In yet some other embodiments, M is a mixture of a transition metal ion and rare earth ion. In some other embodiments, M is Co, Mn, Ni, Dy, Nd, Gd ion, or a combination thereof.

In some embodiments, for the magnetic ionic liquid disclosed herein, Rth and RH are independently a methyl, phenyl, thiophenyl, napthyl, alkyl, or aryl group substituted by one or more electron withdrawing halogens or other groups. In some other embodiments, R$^{10}$ and R$^{11}$ are independently a C1-C4 alkyl group substituted by one or more electron withdrawing halogens or other groups. In some other embodiments, R$^{10}$ and R$^{11}$ are independently a CH$_3$, CHF$_2$, CH$_2$F, or CF$_3$ group. In yet some other embodiments, R$^{10}$ and R$^{11}$ are independently a CF$_3$ group.

In some other embodiments, for the magnetic ionic liquid disclosed herein, the anionic component is [Co(hfacac)$_3$$^-$], [Ni(hfacac)$_3$$^-$], ([Mn(hfacac)$_3$$^-$]), ([Dy(hfacac)$_4$$^-$]), ([Gd(hfacac)$_4$$^-$]), ([Nd(hfacac)$_4$$^-$]), or combination thereof, wherein hfacac is

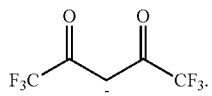

In some embodiments, for the magnetic ionic liquid disclosed herein, the cationic component is [(PR$^1$R$^2$R$^3$R$^4$)$^+$], wherein each of R$^1$, R$^2$, R$^3$, and R$^4$ is independently an unsubstituted or substituted alkyl. In other embodiments, each of R$^1$, R$^2$, R$^3$, and R$^4$ is independently an straight-chain or branched alkyl. In other embodiments, each of R$^1$, R$^2$, R$^3$, and R$^4$ is independently an C$_2$-C$_{20}$ unsubstituted alkyl. In other embodiments, each of R$^1$, R$^2$, R$^3$, and R$^4$ is independently an C$_2$-C$_{20}$ straight-chain or branched alkyl. In some other embodiments, at least one of R$^1$-R$^4$ group is different from the others in the cationic component. In some other embodiments, each of R$^1$, R$^2$, R$^3$, and R$^4$ is independently an C$_2$-C$_{20}$ unsubstituted alkyl, and at least two of R$^1$, R$^2$, R$^3$, and R$^4$ are the same. In yet some other embodiments, each of R$^1$, R$^2$, R$^3$, and R$^4$ is independently an C$_2$-C$_{20}$ unsubstituted alkyl, and three of R$^1$, R$^2$, R$^3$, and R$^4$ are the same. In some other embodiments, each of R$^1$, R$^2$, and R$^3$ is independently a C$_6$ alkyl, and R$^4$ is a C$_{14}$ alkyl. In some other embodiments, each of R$^1$, R$^2$, and R$^3$ is independently a straight-chain C$_6$ alkyl, and R$^4$ is a straight-chain C$_{14}$ alkyl.

In some embodiments, the magnetic ionic liquid disclosed herein is water insoluble, indicated by exhibiting no observable change in color or pH of either the MIL or aqueous phase, or by that the MIL droplets still responded readily to an external magnetic field after three days of suspension in the aqueous phase. In other embodiments, the magnetic ionic liquid disclosed herein has a solubility of less than about 0.01% (v/v) in water. In other embodiments, the magnetic ionic liquid disclosed herein has a solubility of less than about 0.05% (v/v), about 0.04% (v/v), about 0.03% (v/v), about 0.02% (v/v), about 0.009% (v/v), about 0.008% (v/v), about 0.007% (v/v), about 0.006% (v/v), about 0.005% (v/v), about 0.004% (v/v), about 0.003% (v/v), about 0.002% (v/v), about 0.001% (v/v), or any value therein between in water.

In some embodiments, the magnetic ionic liquid disclosed herein has a viscosity of from about 150 cp to about 1,000 cp at the temperature of 23.7° C. In some other embodiments, the magnetic ionic liquid disclosed herein has a viscosity of from about 200 cp to about 950 cp, from about 250 cp to about 900 cp, from about 300 cp to about 850 cp, from about 350 cp to about 800 cp, from about 400 cp to about 750 cp, from about 450 cp to about 700 cp, from about 500 cp to about 650 cp, from about 550 cp to about 600 cp, about 900 cp, about 800 cp, about 700 cp, about 600 cp, about 500 cp, about 400 cp, about 300 cp, about 200 cp, or any value therein between at the temperature of 23.7° C.

In some embodiments, the magnetic ionic liquid disclosed herein has a thermal stability indicated by an onset of decomposition starting at about 110° C. or above. In some embodiments, the magnetic ionic liquid disclosed herein has a thermal stability indicated by an onset of decomposition starting at about 120° C., about 100° C., about 95° C., about 90° C., about 85° C., about 80° C., about 75° C., about 70° C., about 65° C., about 60° C., about 55° C., about 50° C., about 45° C., or any value therein between.

In some embodiments, the magnetic ionic liquid disclosed herein has a magnetic susceptibility from about $2.5\mu_B$ to about $10.0\mu_B$, measured by a Quantum Design MPMS SQUID magnetometer. In some embodiments, the magnetic ionic liquid disclosed herein has a magnetic susceptibility from about $0.5\mu_B$ to about $3.0\mu_B$, from about $2\mu_B$ to about $10\mu_B$, from about $1\mu_B$ to about $5\mu_B$, from about $1\mu_B$ to about $10.0\mu_B$, from about $2\mu_B$ to about $10\mu_B$, from about $3\mu_B$ to about $10.0\mu_B$, from about $1\mu_B$ to about $5\mu_B$, from about $5\mu_B$ to about $10.0\mu_B$, about 10, about 9, about 8, about 7, about 6, about 5, about 4, about 3, about 2, about 1, about 0.5, about 0.2, or any value therein between as measured by a Quantum Design MPMS SQUID magnetometer.

In some embodiments, the magnetic ionic liquid disclosed herein is soluble in hexane, heptane, toluene, and benzene at 10% (v/v) MIL to solvent ratio, in acetone, acetonitrile, chloroform, dichloromethane, dioxane, ethanol, ethyl acetate, diethyl ether, methanol, or isopropyl alcohol at 20% (v/v) MIL to solvent ratio, or in hexane, heptane, toluene, and benzene at 20% (v/v) MIL to solvent ratio.

In some embodiments, the magnetic ionic liquid has a solubility of greater than about 10% (v/v) in an organic solvent (except DMSO). In some other embodiments, the magnetic ionic liquid has a solubility of greater than about 20% (v/v) in an organic solvent (except DMSO). In some other embodiments, the magnetic ionic liquid has a solubility of greater than about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 11% (v/v), about 12% (v/v), about 13% (v/v), about 14% (v/v), about 15% (v/v), about 16% (v/v), about 17% (v/v), about 19% (v/v), or any value therein between in an organic solvent (except DMSO).

In some embodiments, the magnetic ionic liquid disclosed herein can extract a viable bacterium from an aqueous solution comprising the viable bacterium. In some embodiments, the magnetic ionic liquid disclosed herein can preconcentrate a viable bacterium from an aqueous solution comprising the viable bacterium. As used herein, "preconcentrate" means that the bacterium has a higher concentration in the MIL than in the aqueous solution after the MIL is mixed with the aqueous solution.

In some embodiments, the magnetic ionic liquid disclosed herein is not toxic to a bacterium. In some other embodiments, the magnetic ionic liquid disclosed herein is capable of keeping a bacterium viable. As used herein, "viable" means that the bacterium shows no difference in its proliferation, as determined by counting colonies or other routine methods, after being extracted by MILs, when compared to a standard plate in which the bacteria were not exposed to MIL.

In some embodiments, the bacterium is a gram negative bacterium. In some other embodiments, the bacterium is a gram positive bacterium. In yet some other embodiments, the bacterium is *E. coli*. In some other embodiments, the bacterium is *M. smegmatis*.

In another aspect, the present disclosure relates to a method of synthesizing a magnetic ionic liquid, the method comprises mixing ammonium hydroxide, an alcohol, a chelating agent, and metal salt in a reaction vessel for the period of a reaction time at a reaction temperature to produce a corresponding chelated metal anionic component, and mixing a cationic component and the anionic component at a second temperature to produce a magnetic ionic liquid, wherein the metal salt is a paramagnetic transition or rare earth metal salt; the anionic component has the general formula, $[M(Y)_x^-]$, wherein M is transition metal or rare earth metal ion; and the chelating agent comprising a negative ion, Y having the general formula (III),

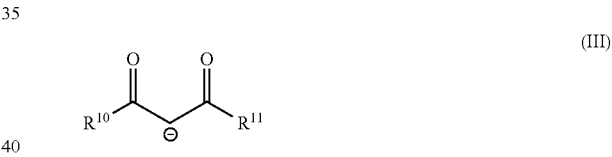

(III)

each of $R^{10}$ and $R^{11}$ is independently a substituted or unsubstituted methyl, phenyl, thiophenyl, napthyl, alkyl or aryl group; and x is 3 or 4; the cationic component is $[(PR^1R^2R^3R^4)^+]$, wherein each of $R^1$, $R^2$, $R^3$, and $R^4$ is independently an unsubstituted alkyl; the vessel is capped, and the chelating agent is added slowly to the vessel containing the alcohol and ammonia hydroxide before the addition of the metal salt.

In some embodiments, the alcohol is ethanol.

In some embodiments, the metal salt is a metal halide salt. In some other embodiments, the metal is a metal chloride salt.

In some embodiments, after the first mixing step starts, any manual or mechanical method can be used during the reaction time to maximize the mixing of the reactants. In some embodiments, vortexing is used. In some embodiments, mechanical stirring is used.

In some embodiments, the reaction time is from about 1 hour to 6 hours. In some other embodiments, the reaction time is from about 30 minutes to 24 hours, about 30 minutes to 1 hours, about 30 minutes to 2 hours, about 30 minutes to 3 hours, about 30 minutes to 4 hours, about 30 minutes to 5 hours, about 30 minutes to 6 hours, about 30 minutes to 7 hours, about 30 minutes to 8 hours, about 30 minutes to 10 hours, about 30 minutes to 12 hours, about 30 minutes to 15 hours, about 30 minutes to 17 hours, about 30 minutes to 20 hours, about 1 hour, about 3 hours, about 5 hours, about 8 hours, about 10 hours, about 15 hours, about 18 hours, about 20 hours, or any value therein between.

In some other embodiments, the reaction temperature or the second temperature is from about 15 to about 40° C. In other embodiments, the reaction temperature or the second temperature is a room temperature, about 10° C., about 15° C., about 20° C., about 25° C., about 30° C., about 35° C., about 40° C., or any value therein between.

In some embodiments, the method of synthesizing MILs disclosed herein, further comprises mixing an alcohol and the chelating agent in the vessel. In some other embodiments, the alcohol used for the synthesis is ethanol.

In some embodiments, for the method of synthesizing MILs disclosed herein, the yield of producing the anionic component is greater than 75%.

In some embodiments, for the method of synthesizing MILs disclosed herein, the produced magnetic ionic liquid is one of the MILs disclosed herein.

In some embodiments, for the method of synthesizing MILs disclosed herein, the metal salt is Dy, Nd, Gd metal chloride, or a combination thereof. In some embodiments, for the method of synthesizing MILs disclosed herein, the metal salt is Dy, Nd, Gd metal chloride, or a combination thereof. In yet some other embodiments, the metal salt is a mixture of a transition metal chloride and rare earth chloride. In some other embodiments, the metal salt is Co, Mn, Ni, Dy, Nd, Gd chloride, or a combination thereof.

In some embodiments, for the method of synthesizing MILs disclosed herein, each of $R^{10}$ and $R^{11}$ is independently a methyl, phenyl, thiophenyl, napthyl, alkyl, or aryl group substituted by one or more electron drawing halogens or other groups. In some other embodiments, each of $R^{10}$ and $R^{11}$ is independently a $C_1$-$C_4$ alkyl group substituted by one or more electron withdrawing halogens or other groups. In some other embodiments, each of $R^{10}$ and $R^{11}$ is independently a $CH_3$, $CHF_2$, $CH_2F$, or $CF_3$ group. In yet some other embodiments, each of $R^{10}$ and $R^{11}$ is independently a $CF_3$ group.

In some other embodiments, for the method of synthesizing MILs disclosed herein, the produced anionic component is $[Co(hfacac)_3^-]$, $[Ni(hfacac)_3^-]$, $([Mn(hfacac)_3^-])$, $([Dy(hfacac)_4^-])$, $([Gd(hfacac)_4^-])$, $([Nd(hfacac)_4^-])$, or combination thereof, wherein hfacac is

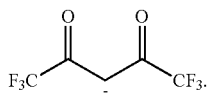

In some embodiments, for the method of synthesizing MILs disclosed herein, the cationic component is $[(PR^1R^2R^3R^4)+]$, wherein each of $R^1$, $R^2$, $R^3$, and $R^4$ is independently an unsubstituted or substituted alkyl. In other embodiments, each of $R^1$, $R^2$, $R^3$, and $R^4$ is independently a straight-chain or branched alkyl. In other embodiments, each of $R^1$, $R^2$, $R^3$, and $R^4$ is independently a $C_2$-$C_{20}$ unsubstituted alkyl. In other embodiments, each of $R_1$, $R^2$, $R^3$, and $R^4$ is independently a $C_2$-$C_{20}$ straight-chain or branched alkyl. In some other embodiments, at least one of $R^1$-$R^4$ group is different from the others in the cationic component. In some other embodiments, each of $R^1$, $R^2$, $R^3$, and $R^4$ is independently a $C_2$-$C_{20}$ unsubstituted alkyl, and at least two of $R^1$, $R^2$, $R^3$, and $R^4$ are the same. In yet some other embodiments, each of $R^1$, $R^2$, $R^3$, and $R^4$ is independently a $C_2$-$C_{20}$ unsubstituted alkyl, and three of $R^1$, $R^2$, $R^3$, and $R^4$ are the same. In some other embodiments, each of $R^1$, $R^2$, and $R^3$ is independently a $C_6$ alkyl, and $R^4$ is a $C_{14}$ alkyl. In some other embodiments, each of $R^1$, $R^2$, and $R^3$ is independently a straight-chain $C_6$ alkyl, and $R^4$ is a straight-chain $C_{14}$ alkyl.

In yet another aspect, the present disclosure relates to a method of extracting, detecting, identifying, quantifying, or a combination thereof a viable bacterium from a sample, the method comprises contacting a sample with a magnetic ionic liquid for the period of a contacting time, wherein the sample comprises a viable bacterium; and the magnetic ionic liquid extracts the bacterium from the sample.

As used herein, "extract" means that the bacterium in the sample migrates onto or into the MIL after the contacting step starts. As used herein, a "sample" can be one originated directly from any food, milk, juice, biological fluid, blood, environmental water, soil, clinical collection, person, or animal, with or without any sample preparation or treatment procedure. A "sample" can also be a mixture of water and a specimen collected from any food, clinical, environmental, human, or animal source that comprises a bacterium. A "sample" can be any specimen that comprises a viable bacterium.

In some embodiments, after the contacting step, any manual or mechanical method can be used during the contact time to maximize the mixing of the MIL and the sample. In some embodiments, vortexing is used. In some embodiments, mechanical stirring is used.

In some embodiments, for the method of extracting, detecting, identifying, quantifying, or a combination thereof a viable bacterium, the magnetic ionic liquid is one of the MILs disclosed herein.

In some embodiments, for the method of extracting, detecting, identifying, quantifying, or a combination thereof a viable bacterium, the magnetic ionic liquid has a higher concentration of the viable bacteria than the sample, after the contacting step. In some embodiments, the ratio of the bacterium concentration in the magnetic ionic liquid to one in the sample is from about 1:1 to about 50:1. In some embodiments, the ratio of the bacterium concentration in the magnetic ionic liquid to one in the sample is from about 1:10 to about 1:1. In some embodiments, the bacterium concentration in the magnetic ionic liquid is higher than one in the sample after the contact time. In some embodiments, the bacterium concentration in the magnetic ionic liquid can be lower than in the sample after the contact time.

In some embodiments, the ratio of the bacterium concentration in the magnetic ionic liquid to one in the sample is from about 1:1 to about 2:1, from about 1:1 to about 5:1, from about 1:1 to about 10:1, from about 1:1 to about 20:1, from about 1:1 to about 30:1, from about 1:1 to about 40:1, about 1:1, about 5:1, about 10:1, about 15:1, about 20:1, about 25:1, about 30:, about 35:1, about 40:1, about 50:1, or any value therein between.

In some embodiments, for the method of extracting, detecting, identifying, quantifying, or a combination thereof a viable bacterium, the weight ratio between the magnetic ionic liquid and the sample is between about 1:10 to 1:100. In some embodiments, for the method of extracting, detecting, identifying, quantifying, or a combination thereof a viable bacterium, the weight ratio between the magnetic ionic liquid and the sample is between about 1:10 to 1:20, between about 1:10 to 1:30, between about 1:10 to 1:40, between about 1:10 to 1:50, between about 1:10 to 1:60, between about 1:70 to 1:80, between about 1:10 to 1:90, between about 10:1 to 1:10, between about 1:20 to 1:50, between about 1:20 to 1:100, between about 1:40 to 1:80, between about 1:50 to 1:10, between about 1:10 to 1:20, about 10:1, about 5:1, about 1:1, about 1:5, about 1:10, about 1:20, about 1:30, about 1:40, about 1:50, about 1:60, about 1:70, about 1:80, about 1:90, about 1:100, or any value therein between.

In some embodiments, for the method of extracting, detecting, identifying, quantifying, or a combination thereof a viable bacterium, the bacterium has a concentration of at least $1.68 \times 10^4$ CFU/mL in the sample.

In some embodiments, for the method of extracting, detecting, identifying, quantifying, or a combination thereof a viable bacterium, the bacterium is a Gram-negative bacterium or Gram-positive bacterium. In some other embodiments, the bacterium is a Gram-negative or *E. coli*. In yet some other embodiments, the bacterium is a Gram-positive bacteria or *M. smegmatis*.

In some embodiments, for the method of extracting, detecting, identifying, quantifying, or a combination thereof a viable bacterium, wherein the sample is a heterogeneous aqueous solution. In some other embodiments, the sample is a heterogeneous aqueous solution comprising food, milk, juices, biological fluid, blood, environmental water or soil, or any suspended solid. In yet some other embodiments, the sample is an aqueous solution comprising food, milk, juice, biological fluid, blood, environmental water, or soil. In some other embodiments, the sample is an aqueous solution comprising or suspended with any material that host a viable bacterium.

In some embodiments, for the method of extracting, detecting, identifying, quantifying, or a combination thereof a viable bacterium, the contact time for the extracting step is from about 30 seconds to about 10 min. In some embodiments, the contact time is from about 1 minute to about 1 hour, from 1 minute to about 2 hours, from 1 minute to about 5 hours, from about 1 hour to 24 hours, about 5 minutes, about 10 minutes, about 2 minutes, about 1 hour, about 2 hours, about 5 hours, about 10 hours, or any value therein between.

In some embodiments, during the contact time, a manual or mechanical method is utilized to maximize the contact between the MIL and the sample for the whole contact time or only for a part of the contact time.

In some embodiments, the method of extracting, detecting, identifying, quantifying, or a combination thereof a viable bacterium further comprises mixing the sample and magnetic ionic liquid during contact time through manual or mechanical agitation after the contacting step starts. Vortexing and hand shaking are examples of agitation to maximize the interaction between the MIL and the sample.

In some embodiments, the method of extracting, detecting, identifying, quantifying, or a combination thereof a viable bacterium further comprises separating the magnetic ionic liquid from the sample by a magnetic field. In some other embodiments, the method further comprises separating the magnetic ionic liquid from the sample by a magnetic field of from about 0.1 tesla to about 2 tesla.

In some embodiments, the method of extracting, detecting, identifying, quantifying, or a combination thereof a viable bacterium further comprises back-extracting the bacterium from the magnetic ionic liquid to a back extraction solution. In some embodiments, the back extraction solution is a nutrient broth, salt solution, or aqueous medium that recovers the bacteria from the MIL as one skilled in the art would employ.

In some embodiments, the method of extracting, detecting, identifying, quantifying, or a combination thereof a viable bacterium further comprises enriching, culturing, or multiplying the bacterium extracted from the sample by the MIL. The techniques are any one of those that would be used by one skilled in the art to increase population of a bacterium.

In some embodiments, the method of extracting, detecting, identifying, quantifying, or a combination thereof a viable bacterium further comprises detecting, identifying, quantifying, or a combination thereof the bacterium.

In some other embodiments, the method further comprises detecting, identifying, quantifying, or a combination thereof the bacterium using PCR amplification in a PCR reagent mixture for a gene or genes in the bacterium. In some other embodiments, the method further comprises detecting, identifying, quantifying, or a combination thereof the bacterium using mass/flow cytometry. In yet some other embodiments, the method further comprises detecting, identifying, quantifying, or a combination thereof the bacterium using a culture-based method.

In some embodiments, the method further comprises detecting, identifying, quantifying, or a combination thereof the bacterium using reverse transcription PCR (RT-PCR) for mRNA in the bacterium. The RT-PCR technique for this purpose is similar to one described in the prior art, such as in "Sheridan, G. E. C., et al. "Detection of mRNA by Reverse Transcription-PCR as an Indicator of Viability in *Escherichia coli* Cells", *Applied and Environmental Microbiology* 64, 4 (1998).

In some embodiments, the method of extracting, detecting, identifying, quantifying, or a combination thereof a viable bacterium has a lower detection limit than the PCR amplification method alone. In some other embodiments, the method has a lower detection limit than a culture based method alone.

Herein, we describe a class of magnetic ionic liquids (MILs) that have very low water solubility, tunable chemical structure, low viscosity, suitable hydrophobicity and greater magnetic susceptibility. Compared to the prior art MILs, the disclosed MILs have improved properties to be used in various applications. One of the unique properties for the disclosed MILs is their ability to isolate, extract, and/or concentrate viable bacteria, such as *E. coli*, from an aqueous sample.

The bacteria extracted or preconcentrated from an aqueous sample using the disclosed MILs can be analyzed by conventional microbiological culture and PCR amplification. However, using the disclosed MILs for extraction or preconcentration can speed up the detection, identification, or quantification of the bacteria, because the MILs can preconcentrate the bacteria or eliminate other factors that might interfere or prevent the detection of the bacteria. By dispersing hydrophobic MILs in an aqueous sample comprising bacteria cells, such as *E. coli* cells, the bacteria can be rapidly extracted and isolated using an applied magnetic field. The extracted cells or derivatives thereof were recovered from the MIL extraction phase by agitation in a nutrient broth and subsequently cultured on selective agar for detection. Interestingly, the enrichment of the bacteria, such as *E. coli* by MILs was dependent upon the identity of the paramagnetic metal incorporated into the chemical structure of the MIL, providing a basis for the design of MILs to exhibit enhanced cell extraction performance. Under optimized conditions, the MIL comprised of a trihexyl(tetradecyl)phosphonium cation ([$P_{6661}^+$]) and Ni(II) hexafluoroacetylacetonate-based anion ([$Ni(hfacac)_3^-$]) was capable of enriching sufficient viable cells for the detection of *E. coli* at concentrations as low as $1.68 \times 10^4$ CFUs mL$^{-1}$ in aqueous solution with an extraction/recovery procedure of less than 10 min. The MIL-based extraction method was also coupled with PCR amplification for the rapid analysis of *E. coli*, demonstrating the compatibility of MILs with both culture-based and nucleic acid-based methodologies for pathogen detection.

Extracting or concentrating bacteria from a complex sample is one of the approaches to improve the existing bacteria testing throughput, since doing so decreases the amount of time to grow the requisite colonies needed for proper identification and quantification. Therefore, extracting or concentrating of bacteria from complex sample matrices using MILs, also called "preconcentration", has great potential applications.

All publications, patent applications, issued patents, and other documents referred to in this specification are indicative of the level of ordinary skill in the art to which this disclosure pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

EXAMPLES

Embodiments of the disclosed MILs and methods are further defined in the following non-limiting Examples. These Examples, while indicating certain embodiments of the disclosed MILs and methods, are given by way of illustration only and should not be considered as limiting in any way. From the above discussion and these Examples, one skilled in the art can ascertain the essential characteristics of this disclosure, and without departing from the spirit and scope thereof, can make various changes and modifications of the embodiments of the disclosed MILs and methods to adapt it to various usages and conditions. Thus, various modifications of the embodiments of the disclosed MILs and methods, in addition to those shown and described herein, will be apparent to those skilled in the art from the foregoing description. Such modifications are also intended to fall within the scope of the appended claims.

Materials and Methods

Reagents and Materials

The reagents, ammonium hydroxide (28-30% solution in water) and 1,1,1,5,5,5-hexafluroacatelyacetone (99%), were purchased from Acros Organics (Morris Plains, N.J., USA). Gadolinium(III) chloride hexahydrate (99.9%) and manganese(II) chloride tetrahydrate (98.0-101.0%) were purchased from Alfa Aesar (Ward Hill, Mass., USA). Acetonitrile (99.9%), hexane (98.5%), methanol (99.9%), cobalt(II) chloride hexahydrate (98%), dysprosium(III) chloride hexahydrate (99.9%), nickel(II) chloride (98%), and neodymium (III) chloride hexahydrate were purchased from Sigma Aldrich (St. Louis, Mo., USA). Anhydrous diethyl ether (99.0%) was purchased from Avantor Performance Materials Inc. (Center Valley, Pa., USA). Ethanol (100%) was purchased from Decon Labs (King of Prussia, Pa., USA). Deuterated DMSO was obtained from Cambridge Isotope Laboratories (Andover, Mass., USA). All solvents and reagents were used as received without any additional drying or purification. Deionized water (18.2 MS2 cm) was obtained from a Milli-Q water purification system (Millipore, Bedford, Mass., USA). Trihexyl(tetradecyl)phosphonium chloride (>93%) was purchased from Strem Chemical (Newburyport, Mass., USA). Trihexyl(tetradecyl)phosphonium chloride was further purified by dissolving 20 g of the IL in 50 mL of acetonitrile. The acetonitrile layer was washed three times with 5 mL aliquots of hexane. Acetonitrile was subsequently evaporated off under reduced pressure followed by drying of the IL at 50° C. in a vacuum oven.

Nickel(II) chloride and hexafluoroacetylacetone were purchased from Acros Organics (NJ, USA) with gadolinium (III) chloride hexahydrate and manganese(II) chloride tetrahydrate were obtained from Alfa Aesar (Haverhill, Mass., USA). Cobalt(II) chloride hexahydrate, dysprosium(III) chloride hexahydrate, and neodymium(III) hexahydrate were purchased from Sigma Aldrich (St. Louis, Mo., USA). NEB-5a Competent *E. coli* cells (K12 strain) with Super Optimal Broth with Catabolite Repression (SOC) outgrowth medium and Phusion High Fidelity DNA Polymerase were purchased from New England Biolabs (Ipswich, Mass., USA). dNTPs were obtained from Thermo Scientific (Wilmington, Del., USA). Modified pET-32 plasmid was obtained from EMD Millipore (Billerica, Mass., USA) and primers for PCR amplification were purchased from IDT (Coralville, Iowa, USA). Miller's luria broth (LB) and agar for microbiological cultures were purchased from Fisher Scientific (Fair Lawn, N.J., USA). Carbenicillin, agarose, tris(hydroxymethyl)aminomethane and a 1 kb plus DNA ladder were purchased from P212121 (Ypsilanti, Mich., USA). SYBR Safe DNA gel stain was obtained from Life Technologies (Carlsbad, Calif., USA). All stock solutions and dilutions were made using deionized water (18.2 MS2 cm) from a Milli-Q water purification system (Millipore, Bedford, Mass., USA).

Instrumentation

Proton NMR spectra ($^1$H) were recorded using a Bruker 500 MHz nuclear magnetic resonance spectrometer. Solvent peaks were used as reference values for the reporting of chemical shifts. Elemental analyses were obtained using a Perkin Elmer 2100 Series II CHN/S Analyzer (Waltham, Mass., USA). Mass spectra were obtained using an Agilent 6230 TOF LC/MS (Santa Clara, Calif., USA). Viscosity measurements were obtained using a Wells/Brookfield DV1 cone and plate viscometer using a CPA-51Z cone spindle. Each MIL was dried in a vacuum oven for 48 hours at 50° C. ensuring any water or residual solvents were completely removed from the MILs. Sample volumes of 0.5 mL were used for all MILs at a temperature (23.7° C.).

All cell cultures were grown in an I24R incubator shaker (New Brunswick Scientific, Enfield, Conn., USA) with a Horizon Plasmafuge-6 (Fisher Scientific) subsequently used for cell harvesting. Vortex agitation was applied to cell suspensions and samples with a Barnstead/Thermolyne Type 16700 Mixer (Dubuque, Iowa, USA). A NanoDrop 2000c spectrophotometer (Thermo Scientific, Wilmington, Del., USA) was used to measure the optical density of aqueous cell suspensions. A Mettler Toledo NewClassic MF MS105 (readability=0.01 mg) microbalance was used to measure the mass of MILs. PCR experiments were conducted using a Techne FTgene2D thermal cycler (Burlington, N.J., USA) and gel electrophoresis performed on a BRL H4 Horizontal Gel Electrophoresis system (Life Technologies) using a dual output power supply (Neo/Sci, Rochester, N.Y., USA). A Safe Imager 2.0 transilluminator (Invitrogen) was used for the visualization of all agarose gels. A 0.9 T cylindrical magnet purchased from K&J magnetics (Pipersville, Pa., USA) was used to manipulate the MIL extraction solvent during extraction procedures. Colonies were cultured on LB agar plates using a Barnstead/Thermolyne Type 142300 Incubator.

Transformation and Cell Cultures

Competent *E. coli* cells were transformed with modified pET-32 plasmid DNA (pDNA) containing the 5'-methylthioadenosine phosphorylase (MTAP) gene. Briefly, 20 μL of competent cells were thawed on ice for 10 min and spiked with 94.5 ng of pDNA. After the sample tube was gently flicked and placed on ice for 30 min, the mixture was subjected to heat shock at 42° C. for 30 s and once again chilled on ice for 5 min. The cell suspension was mixed with 950 μL of room temperature SOC outgrowth medium and the mixture incubated at 37° C. for 60 min. The transformed cells were then cultured in 5 mL of LB media containing 100 μg mL$^{-1}$ carbenicillin for 24 h. A 500 μL aliquot of the culture was mixed with 500 μL of sterile 50% glycerol (v/v) and stored at −80° C. for later use.

For each cell extraction experiment, 2 mL of sterile LB media with 100 μg mL$^{-1}$ carbenicillin was inoculated with 0.5 μL of *E. coli* glycerol stock and incubated overnight at 37° C. and 225 rpm. The overnight culture was centrifuged at 2820 g for 8 min and the supernatant discarded. The cells were then vortexed for 15 s in 2 mL of deionized water and centrifuged once again at 2820 g for 8 min. Following a total of three washes, the cells were re-suspended in 1 mL of deionized water. The concentration of cells within the suspension was initially determined by measuring the optical density of the sample at 600 nm (OD600), where an OD600 equal to 1.000 represents 8×10$^8$ *E. coli* cells mL$^{-1}$. The bacterial suspension was diluted to an OD600 value of 0.021 (1.68×107 cells mL$^{-1}$), after which 10-fold serial dilutions were performed to yield the desired sample concentration. Since the sample concentrations were below the detection limit of the spectrophotometer, the final concentration of each sample (in CFUs mL$^{-1}$) was obtained using a plate counting method. Briefly, 15 μL of diluted cell suspension were mixed with 985 μL of LB media and vortexed for 3 min. A 1004 aliquot of the suspension was spread onto a selective LB agar plate with 100 μg mL$^{-1}$ carbenicillin and incubated overnight at 37° C. to obtain visible colonies.

MIL-Based Whole Cell Extraction

Figure 10:
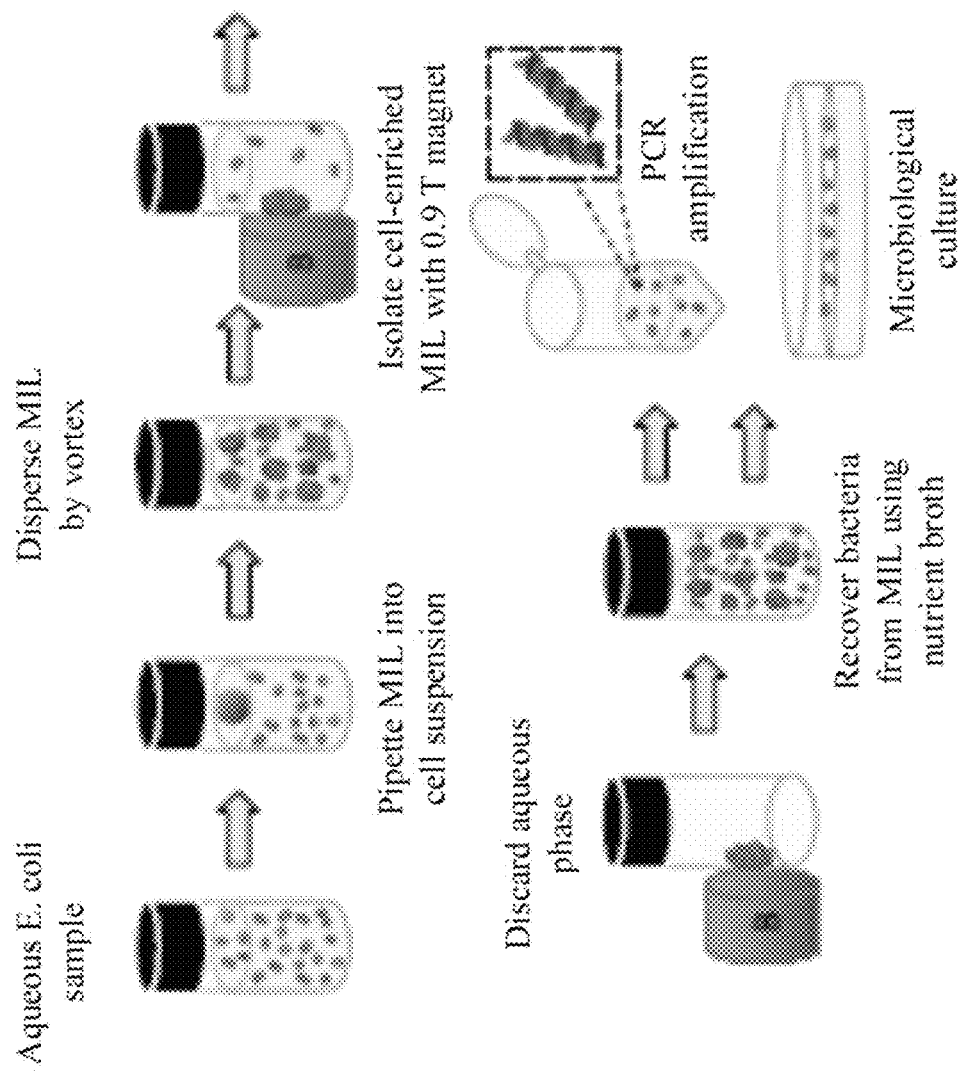
FIG. 10 shows a general schematic for the MIL-based cell extraction procedure to extract and preconcentrate exemplary E. coli from an aqueous sample followed by recovery of the E. coli cells from the MIL phase and subsequent PCR amplification or microbiological culture for its identification and quantification.

A general schematic for the MIL-based cell extraction procedure is depicted in FIG. 10. In a 4 mL screw cap glass vial, a controlled volume (e.g., 10 μL) of MIL was added to 2 mL of diluted cell suspension and dispersed into microdroplets by vortex agitation for 15-120 s. Following the dispersive extraction, a 0.9 T magnetic field was applied to collect the cell-enriched MIL extraction phase. After the aqueous phase was decanted, the MIL was subjected to a static wash with 2 mL of deionized water to ensure that residual cell suspension was removed. The extracted *E. coli* was recovered from the MIL solvent by vortexing the MIL in 1 mL of LB media from 30 to 300 s. Following back-extraction, aliquots of the cell-enriched LB media were cultured on selective agar as well as analyzed by PCR.

Selective Culture and Colony Enumeration

To detect viable bacteria recovered from the MIL extraction solvent, a culture-based method selective for *E. coli* transformants was employed. Following MIL-based extraction, a 100 μL aliquot of the LB back-extraction solution was plated on LB agar containing 100 μg mL$^{-1}$ carbenicillin and incubated overnight at 37° C. Visible colonies were counted, tabulated, and compared to the colonies obtained for the sample prior to extraction. The enrichment factor ($E_F$) from the MIL-based extraction was calculated by Equation 1, where $C_{MIL}$ is the concentration of CFUs within the MIL extraction phase and $C_S$ represents the concentration of CFUs in the bacterial suspension prior to extraction.

$E_F = C_{MIL}/C_S$  Equation 1

The volume of MIL used for the calculation of $C_{MIL}$ was determined from the mass of the MIL transferred into the sample solution prior to extraction and the density of the MIL.

PCR and Gel Electrophoresis

Following the recovery of *E. coli* cells from the MIL extraction phase, an aliquot of the LB back-extraction solution was analyzed by PCR. Briefly, a 1 μL aliquot of cell-enriched LB back-extraction solution was mixed with 35.5 μL of deionized water, 10 μL of 5× Phusion HF buffer, 0.2 mM dNTP mix, 1 U of Phusion DNA polymerase, and 0.2 μM of each primer resulting in a total reaction volume of 50 μL. Primers for amplification of the 879 bp MTAP gene from pDNA were 5' TGC TGT TCC AGG GAC CT 3' and 5' GAA TTC GGA TCC GGA CGC 3'. The thermal protocol used for amplification of the MTAP gene was as follows: 5 min initial denaturation at 95° C. followed by 30 cycles of 30 s denaturation at 95° C., 45 s annealing at 54° C., and elongation for 45 s at 72° C.

After thermal cycling, the PCR products were mixed with 10 μL of bromophenol blue tracking dye solution (30% glycerol v/v) and loaded on a 1% agarose gel stained with SYBR Safe DNA gel stain. The PCR amplicon was subjected to electrophoresis at approximately 4 V cm$^{-1}$ and subsequently visualized using a transilluminator.

Example 1

Preparation of Exemplary Transition Metal Based MILs

Transition or rare earth metal based MILs are usually synthesized according to the steps in Scheme 1.

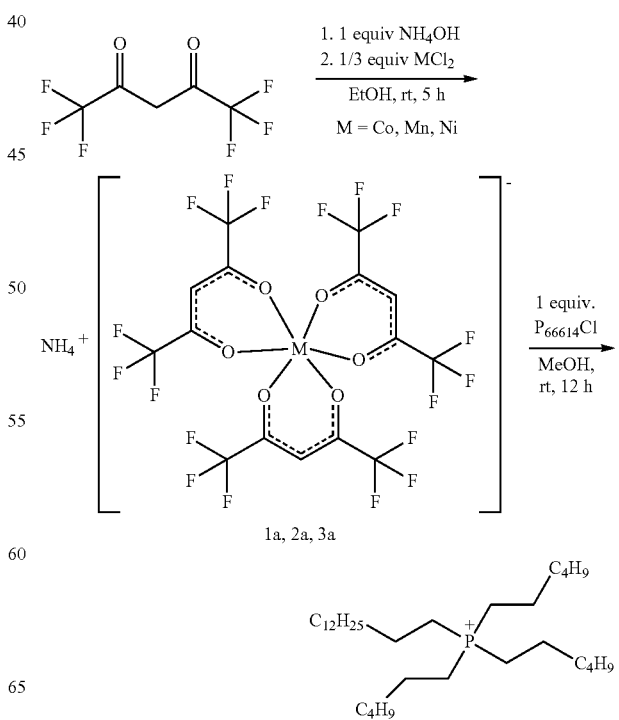

Scheme 1. Synthesis of transition metal and rare earth-based magnetic ionic liquids

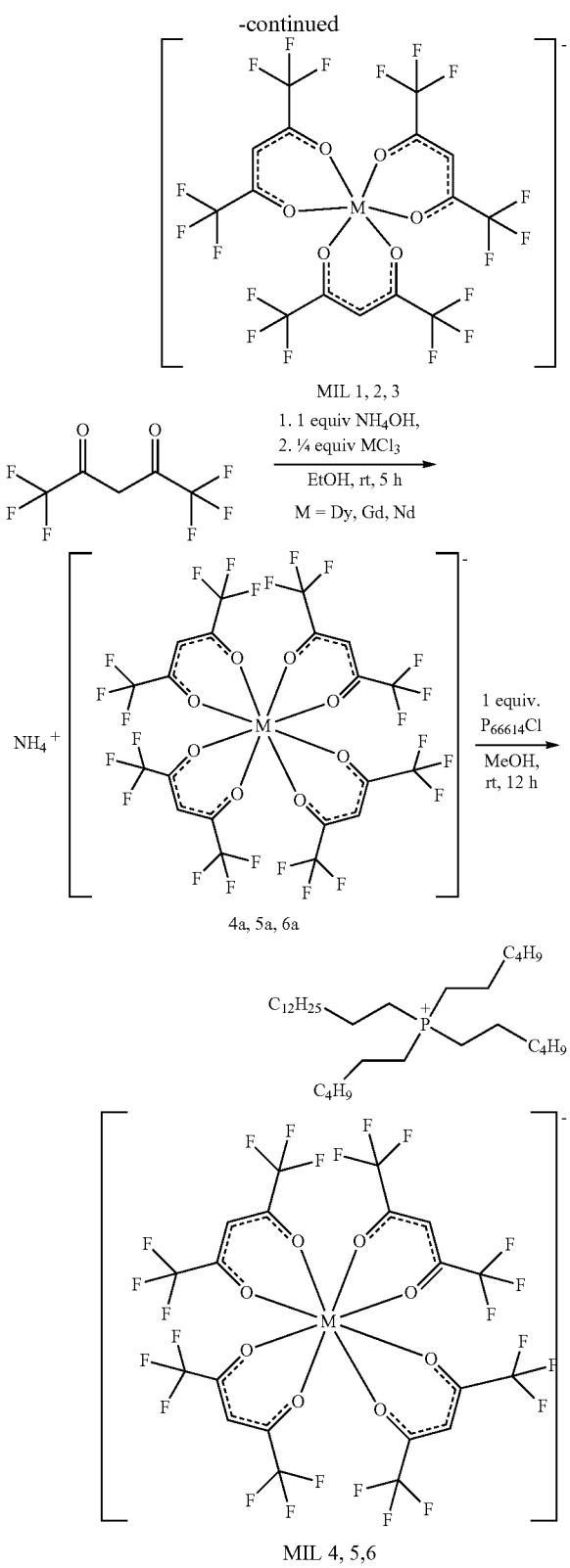

MIL 1, 2, 3

MIL 4, 5, 6

The exemplary MILs synthesized in this Examples section comprise heavily alkylated phosphonium-based cations, i.e., [$P_{66614}^+$], exhibit high hydrophobicity with relatively low melting points due largely to its asymmetry. The [$P_{66614}^+$][$Cl^-$] IL is commercially available. As shown in Scheme 1, reaction of ammonium hexafluoroacetylacetonate ([$NH_4^+$][$hfacac^-$]) with various transition and rare earth metal centers yields the hydrophobic ammonium-based salt intermediates 1a-6a that do not dissolve in water, even at very high ratios of water to salt.

Pairing of intermediate 1a to an imidazolium-based cation was carried out for preliminary viscosity and hydrophobicity testing. A metathesis reaction was performed between 1-(6-hydroxyhexyl)-3-methylimidazolium chloride [$MC_6OHIM^+$][$Cl^-$] and intermediate 1a to form [$MC_6OHIM^+$] [$Co(hfacac)_3^-$]. The resulting MIL was soluble in water as determined by an obvious color change in the aqueous solution two hours after addition of the MIL. Furthermore, the neat MIL could not be transferred with a pipette at room temperature due to its high viscosity. Pairing the cation of the hydrophobic ammonium-based Aliquat 336 with intermediate 1a also resulted in a very viscous MIL that could not be drawn into a pipette. Since the broad applicability of hydrophobic MILs is very much dependent upon the ease with which they can be transferred using traditional liquid handling methods, the [$P_{66614}^+$] cation was selected for preparation of the hfacac-based MILs.

Previously, transition metal hexafluoroacetylacetonate MILs were created in two different synthetic pathways, both involving a three-step synthesis (H. Mehdi, K. Binnemans, K. Van Hecke, L. Van Meervelt and P. Nockemann, Chem. Commun., 2010, 46, 234-236 and P. Zhang, Y. Gong, Y. Lv, Y. Guo, Y. Wang, C. Wang and H. Li, Chem. Commun., 2012, 48, 2334-2336). In this disclosure, the creation of metal salts 1a-6a (Scheme 1) was achieved in a one-pot synthesis by reacting ammonium hydroxide, hexafluoroacetylacetone, and the metal chloride salt. Reaction yields greater than 81% were achieved after 5 hours of total reaction time. It is important to highlight in this synthesis method the need to add hexafluoroacetylacetone slowly, such as to add via a syringe, to the capped reaction vessel containing ethanol and ammonium hydroxide. The acid-base reaction between hexafluoroacetylacetone and ammonium hydroxide causes a vapor to form inside the reaction vessel. Loss of this vapor resulted in low product yields <20%, presumably due to the vaporization of both hexafluoroacetylacetone and ammonium hydroxide (which have boiling points <75° C.).

Exemplary transition metal based MILs 1-3 were synthesized by dissolving 10 mmol of ammonium hydroxide in 30 mL of ethanol. The reaction vessel was then sealed with a rubber septum and 10 mmol of hexafluoroacetylacetone was added dropwise to the reaction via syringe. A white vapor was allowed to settle before adding 3.3 mmol of cobalt(II) chloride hexahydrate. The reaction was allowed to stir at room temperature for 5 hours. The solvent was removed under reduced pressure and the crude product was redissolved in 20 mL of diethyl ether and washed several times with 5 mL aliquots of deionized water until the aqueous fraction yielded no precipitate during a $AgNO_3$ test. Diethyl ether was evaporated and the anion was allowed to dry at 50° C. overnight under reduced pressure. 1 mmol of the anion was added to 1 mmol of purified phosphonium chloride and dissolved in 30 mL of methanol. This reaction was allowed to stir overnight at room temperature. The solvent was evaporated and 20 mL of diethyl ether was added to dissolve the crude product. The ether layer was washed several times with 5 mL aliquots of deionized water until the aqueous fraction yielded no precipitate during an $AgNO_3$ test. Ether was evaporated off and MIL 1 was dried at 50° C. overnight under reduced pressure. For MILs 2 and 3, the same procedure was followed using manganese(II) chloride tetrahydrate and nickel(II) chloride, respectively.

The characterization of the intermediates and MILs are the following:

1a: Red solid. Yield 82%. TOF LC/MS: m/z (−) 680.4.
2a: Yellow solid. Yield 79%. TOF LC/MS: m/z 676.4.
3a: Green solid. Yield 81%. TOF LC/MS: m/z (−) 679.4.
MIL 1: Dark red viscous liquid. Yield 92%. Elem. anal. calcd (%) $C_{47}H_{71}CoF_{18}O_6P$: C, 48.50; H, 6.15; N, 0. Found: C, 49.09; H, 6.31; N, 0.03. TOF LC/MS: m/z (+) 483.4; (−) 680.4.
MIL 2: Light orange viscous liquid. Yield 91%. Elem. anal. calcd (%) $C_{47}H_{71}MnF_{18}O_6P$: C, 48.67; H, 6.17; N, 0. Found: C, 48.89; H, 6.22; N, 0.37. TOF LC/MS: m/z (+) 483.4; (−) 676.4.
MIL 3: Dark green viscous liquid. Yield 90%. Elem. anal. calcd (%) $C_{47}H_{71}NiF_{18}O_6P$: C, 48.51; H, 6.15; N, 0. Found: C, 48.72; H, 6.22; N, 0.27. TOF LC/MS: m/z (+) 483.4; (−) 679.4.

The synthesis of the chelated metal salt was followed by a metathesis reaction between intermediates 1a-3a and ($[P_{66614}^+][Cl^-]$), thereby producing transition metal-based MILs 1-3 (Scheme 1) in a total of two steps.

Example 2

Preparation of Exemplary Rare Earth Based MILs

MILs 4-6 were synthesized by dissolving 10 mmol of ammonium hydroxide in 30 mL of ethanol. The reaction vessel was then sealed with a rubber septum and 10 mmol of hexafluoroacetylacetone was added dropwise to the reaction via syringe. A white vapor was allowed to settle before adding 2.5 mmol of dysprosium(III) chloride hexahydrate. The reaction was allowed to stir at room temperature for 5 hours. The solvent was removed under reduced pressure and the crude product was redissolved in 20 mL of diethyl ether and washed several times with 5 mL aliquots of deionized water until the aqueous fraction yielded no precipitate during an $AgNO_3$ test. Diethyl ether was evaporated and the anion was allowed to dry at 50° C. overnight under reduced pressure. 1.2 mmol of the anion salt was added to 1 mmol of purified phosphonium chloride and dissolved in 30 mL of methanol. This reaction was allowed to stir overnight at room temperature. The solvent was evaporated and 10 mL of hexane was added to the crude product to precipitate out any unreacted anion salt and filtered off. Once more, the solvent was evaporated and 20 mL of diethyl ether was added to dissolve the crude product. The ether layer was washed several times with 5 mL aliquots of deionized water until the aqueous fraction yielded no precipitate during an $AgNO_3$ test. Ether was evaporated off and MIL 4 was dried at 50° C. overnight under reduced pressure. For MILs 5 and 6, the same procedure was followed using gadolinium(III) chloride hexahydrate and neodymium(III) chloride hexahydrate, respectively.

The characterization of the intermediates and MILs are the following:

4a: White solid. Yield 83%. TOF LC/MS: m/z (−) 992.7.
5a: White solid. Yield 82%. TOF LC/MS: m/z (−) 986.7.
6a: Pink solid. Yield 81%. TOF LC/MS: m/z (−) 972.6.
MIL 1: Light gold viscous liquid. Yield 93%. Elem. anal. calcd (%) $C_{52}H_{72}DyF_{24}O_8P\cdot2H_2O$: C, 41.35; H, 5.07; N, 0. Found: C, 41.39; H, 4.74; N, 0.25 TOF LC/MS: m/z (+) 483.4; (−) 992.7.
MIL 5: Light yellow viscous liquid. Yield 91%. Elem. anal. calcd (%) $C_{52}H_{72}GdF_{24}O_8P\cdot2H_2O$: C, 41.49; H, 5.09; N, 0. Found: C, 41.85; H, 4.67; N, 0.31 TOF LC/MS: m/z (+) 483.4; (−) 986.7.
MIL 6: Light pink viscous liquid. Yield 90%. Elem. anal. calcd (%) $C_{52}H_{72}NdF_{24}O_8P\cdot2H_2O$: C, 41.85; H, 5.13; N, O. Found: C, 41.82; H, 4.53; N, 0.28 TOF LC/MS:m/z (+) 483.4; (−) 972.6.

The chelation of hexafluoroacetylacetone to neodymium was also previously reported and although the crystal structure was isolated, the synthesis was limited by the solubility of the cation in the aqueous phase (H. Mehdi, K. Binnemans, K. Van Hecke, L. Van Meervelt and P. Nockemann, *Chem. Commun.*, 2010, 46, 234-236). Furthermore, the reported procedure required reaction of the rare earth oxide $NdO_3$ with bis(trifluoromethane)sulfonamide ($HNTf_2$), an expensive reagent when compared to hexafluoroacetylacetone. To circumvent the limitations of this reaction, a synthesis similar to the transition metal analogues (Scheme 1) was followed to produce intermediates 4a-6a after five hours in yields greater than 80%. A subsequent metathesis reaction between 4a-6a and $[P_{66614}^+]$ $[Cl^-]$ generated MILs 4-6 (Scheme 1). This synthetic strategy allows for the incorporation of rare earth metal centers possessing higher magnetic susceptibility, such as gadolinium and dysprosium, in a two-step synthesis.

Example 3

Evaluation of Exemplary MILs
Water Solubility

The water solubility of these exemplary MILs was tested by pipetting a 1 μL droplet of MIL into 10 mL of deionized water to create a 0.01% (v/v) solution. After pipetting the MIL into the aqueous sample, the MIL was observed to form a wide droplet that rests on top of the solution. Vortexing the MIL droplet caused dispersion of the MIL into fine microdroplets that were suspended within the aqueous solution, ultimately settling at the bottom of the vessel. The aqueous solution exhibited no observable change in color or pH, and the MIL droplets still responded readily to an external magnetic field after three days of suspension in the aqueous phase. These are all highly attractive features required in the design of low viscosity, hydrophobic MILs that possess high magnetic susceptibility. To demonstrate the hydrophobicity of these MILs compared to other available hydrophobic MILs, 50 μL of $[P_{66614}^+][FeCl_4^-]$, $[P_{66614}^+][Co(hfacac)_3^-]$, and $[P_{66614}+][Nd(hfacac)_4^-]$ were pipetted into separate scintillation vials containing 12 mL of deionized water. Each MIL was vortexed and heated to 85° C. for 10 minutes. FIG. 1 shows a solution of the $[P_{66614}+][FeCl_4^-]$ MIL dissolving into the aqueous solution noted by discoloration while both $[P_{66614}^+][Co(hfacac)_3^-]$ and $[P_{66614}^+][Nd(hfacac)_4^-]$ MILs exhibit no sign of dissolution into the aqueous phase.

Solvent Miscibility

Owing to their unique solvation capabilities and high thermal stability, ILs have been successfully employed in organic synthesis either as reaction media or catalysts. An evaluation of the hydrophobic MIL solubility in a wide range of organic solvents may provide a fundamental understanding into their solvent properties. This could be instrumental for designing MIL-based reaction media, where the MIL can be selectively separated from the reaction products using an external magnetic field. The solubility of the MILs prepared in this study were tested in 15 different organic solvents possessing a wide range of polarities. Table 1 shows the solubility of each exemplary MIL in the different organic solvents. The transition-metal based MILs (MILs 1-3) were fully miscible in all of the organic solvents except DMSO. A trend can be observed that the transition metal-based MILs show full miscibility in solvents with Reichardt's polarity index values ranging from 0.117 (ethyl ether)-0.762 (methanol) at a 20% (v/v) MIL to solvent ratio, with the exception of DMSO. However, as the polarity value of the solvent drops below 0.117, the transition-metal based MILs show decreased solubilities at a 10% (v/v) MIL to solvent ratio. All of the transition metal-based MILs exhibited some solubility in DMSO, however, it was observed that fine droplets of insoluble MIL remain at a 10% (v/v) MIL to solvent ratio. The rare earth-based MILs were miscible in all of the tested solvents at a 20% (v/v) MIL to solvent ratio. Furthermore, the rare earth-based MILs exhibit higher solubility in non-polar solvents such as benzene, toluene, heptane, and hexane when compared to the transition metal-based MILs. The solubility of these MILs in many different organic solvents adds to their versatility and use in numerous applications.

TABLE 1

Physicochemical and Magnetic Properties of Transition and Rare Earth Metal-based MILs

| MIL | Abbreviation | MW (g/mol) | Viscosity (cP)$^a$ | Solubility | $\mu_{eff}$ ($\mu_B$) |
|---|---|---|---|---|---|
| 1 | [$P_{66614}^+$][Co(hfacac)$_3^-$] | 1164.0 | 575.8 | S$^{b,c,e}$ | 4.3 |
| 2 | [$P_{66614}^+$][Mn(hfacac)$_3^-$] | 1160.0 | 401.8 | S$^{b,c,e}$ | 5.8 |
| 3 | [$P_{66614}^+$][Ni(hfacac)$_3^-$] | 1163.7 | 927.9 | S$^{b,c,e}$ | 2.8 |
| 4 | [$P_{66614}^+$][Dy(hfacac)$_4^-$] | 1474.6 | 291.5 | S$^{c,d,e}$ | 9.7 |
| 5 | [$P_{66614}^+$][Gd(hfacac)$_4^-$] | 1469.3 | 276.5 | S$^{c,d,e}$ | 7.7 |
| 6 | [$P_{66614}^+$][Nd(hfacac)$_4^-$] | 1456.3 | 299.4 | S$^{c,d,e}$ | 2.8 |

$^a$Viscosity measurements were performed at 23.7° C.
$^b$Soluble in hexane, heptane, toluene, and benzene at 10% (v/v) MIL to solvent ratio.
$^c$Soluble in acetone, acetonitrile, chloroform, dichloromethane, dioxane, ethanol, ethyl acetate, diethyl ether, methanol, isopropyl alcohol at 20% (v/v) MIL to solvent ratio.
$^d$Soluble in hexane, heptane, toluene, and benzene at 20% (v/v) MIL to solvent ratio.
$^e$Insoluble in water at 0.01% (v/v) MIL to water ratio.

$\mu_{eff}$ = effective magnetic moment in Bohr magnetons ($\mu_B$) determined from magnetic susceptibility data (from Quantum design SQUID magnetometer).

Viscosity

Figure 2:
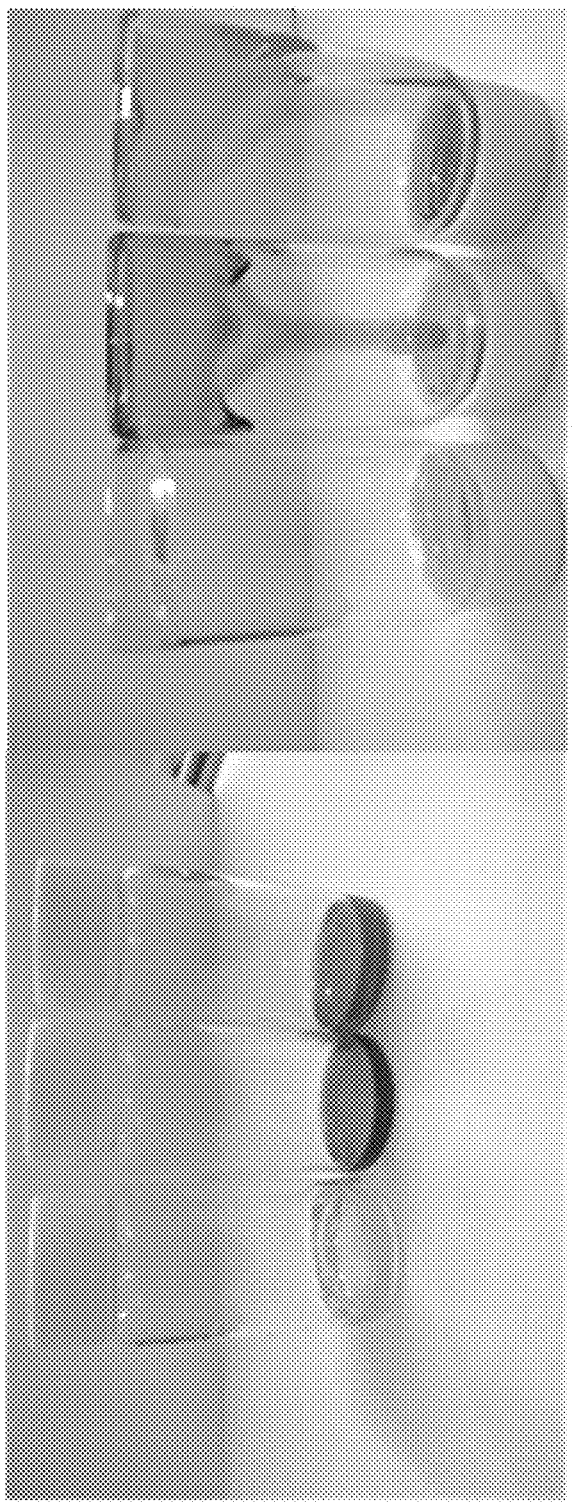
FIG. 2 shows $[P_{66614}^+]_2[MnCl_4^{2-}]$ (left), $[P_{66614}^+][Ni(hfacac)_3^-]$ (middle), and $[P_{66614}^+][Nd(hfacac)_4^-]$ (right) in a vial before and after inversion for 1 second.

Many previously synthesized hydrophobic MILs such as [$P_{66614}^+$] tetrachloromanganate(II) ([$P_{66614}^+$]$_2$[MnCl$_4^{2-}$]), [$P_{66614}^+$] tetrachloroferrate(III) ([$P_{66614}^+$][FeCl$_4^-$]), and [$P_{66614}$] hexachlorogadolinate(III) ([$P_{66614}^+$]$_3$[GdCl$_6^{3-}$]) possess high viscosities ranging from 650-83450 cP at 25° C., which can be problematic when using them for a number of applications. In this disclosure, a strategy was implemented to lower the viscosity by creating a singly charged metal anion paired with a cation that has previously been shown to produce MILs with low viscosity. The [$P_{66614}^+$][FeCl$_4^-$] MIL possesses a viscosity of 650 cP at 25° C., which is much lower compared to the [$P_{66614}^+$]2[MnCl$_4^{2-}$] (75230 cP at 25° C.) and [$P_{66614}^+$]$_3$[GdCl$_6^{3-}$] (18390 cP at 25° C.) MILs. The use of a β-diketonate ligand allows for an overall singly charged anion as well as high spin states for some of the metal centers. Viscosities of the exemplary MILs disclosed herein are given in Table 1. The transition metal-based MILs all exhibit higher viscosities than the rare earth MILs, with the highest viscosity of 927 cP measured for the nickel-based MIL. An increasing trend of viscosities for the transition-metal MILs can be observed with a decrease in atomic radii from manganese to nickel (401.8 cP-927.9 cP). The rare earth metal MILs possess exceedingly low viscosities at 23.7° C. (<300 cP) when compared to other [$P_{66614}$] based MILs such as [$P_{66614}^+$][FeCl$_4^-$] and [$P_{66614}^+$]$_2$[MnCl$_4^{2-}$]. FIG. 2 compares the viscosities of [$P_{66614}^+$]$_2$[MnCl$_4^{2-}$], [$P_{66614}^+$][Ni(hfacac)$_3^-$], and [$P_{66614}^+$][Nd(hfacac)$_4^-$] by performing a 1 second inversion of each MIL. The [$P_{66614}^+$]$_2$[MnCl$_4^{2-}$] MIL exhibits little to no movement down the vial due to its high viscosity while the [$P_{66614}^+$][Ni(hfacac)$_3^-$] and [$P_{66614}^+$][Nd(hfacac)$_4^-$] MILs flow easily toward the bottom of the vial. It should also be noted that all of the studied hexafluoroacetylacetonate-based MILs could be easily pipetted at room temperature without heating.

Thermal Stability

The thermal stability of all exemplary MILs was tested by monitoring the thermal volatilization/decomposition of the MIL when the MIL was used as a stationary phase in gas chromatography. To achieve this, an approximate 0.25-0.28 μm film of IL/MIL was immobilized on the inner wall of a fused silica capillary. The IL/MIL coated capillary was then heated slowly in a GC oven and an ultra-sensitive flame ionization detector (FID) was used to detect any volatilization/decomposition of the IL/MIL. These tests were run using a temperature program starting at 40° C. and increased at 1° C./min to 350° C. on an Agilent 6850 gas chromatograph with a flame ionization detector (Santa Clara, Calif., USA). The [$P_{66614}^+$] [Cl$^-$] IL was also coated under the same conditions and was used as a reference.

Figure 3:
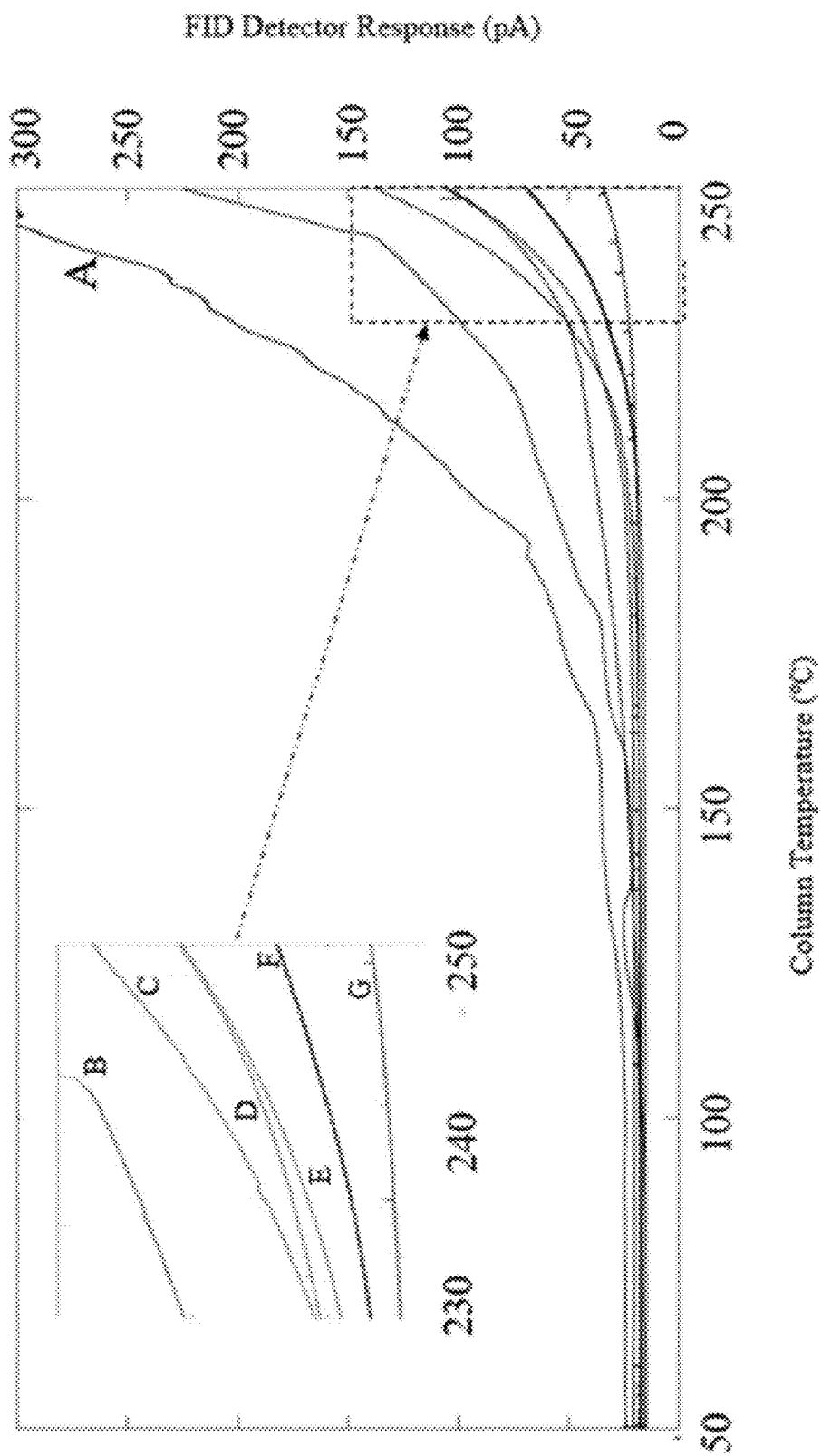
FIG. 3 shows the thermal stability diagram constructed by coating a thin layer of MIL on the wall of fused silica capillary followed by heating under a constant flow of helium and detecting any volatilization/decomposition products using an ultra-sensitive flame ionization detector. A magnified inset from 230 to 250° C. is shown at the top left for clarity purposes.

FIG. 3 shows the thermal stability diagram of each MIL as the temperature of the MIL within the capillary column is steadily increased. A magnified inset from 230 to 250° C. is shown at the top left of FIG. 3 for clarity purposes. In FIG. 3, (A) represents for [$P_{66614}^+$] [Co(hfacac)$_3^-$]; (B) for [$P_{66614}^+$][Mn(hfacac)$_3^-$]; (C) for [$P_{66614}^+$][Gd(hfacac)$_4^-$]; (D) for [$P_{66614}^+$][Dy(hfacac)$_4^-$]; (E) for [$P_{66614}^+$][Ni(hfacac)$_3^-$]; (F) [$P_{66614}^+$][Nd(hfacac)$_4^-$]; and (G) for [$P_{66614}^+$] [Cl$^-$]. The reference column containing the [$P_{66614}^+$] [Cl$^-$] IL produced the lowest thermal decomposition indicating that the presence of the metal anion complex limits the thermal stability of the MILs. The cobalt-based MIL showed the lowest thermal stability, with the onset of decomposition starting at approximately 130° C. and a sharp increase in the rate of decomposition occurring around 200° C. The manganese-based MIL exhibited a similar profile with its degradation starting approximately 25° C. higher than the cobalt-based MIL. Conversely, the neodymium-based MIL showed the highest thermal stability out of all the MILs tested with slight and gradual degradation beginning around 225° C. Gadolinium, dysprosium, and nickel-based MILs all exhibited similar thermal stabilities with more rapid decomposition of the MIL occurring above 215° C.

Magnetic Susceptibility

Exemplary MILs possess paramagnetic behavior that provides them distinct advantages over traditional ILs by allowing them to be easily removed or separated from an immiscible phase through the application of an external magnetic field. A handheld 1/16"×1" neodymium-based rod magnet with a surface field of 6597 Gauss is sufficiently strong to collect small droplets of MIL dispersed in aqueous media. Octahedral complexes of Co(II), Mn(II), and Ni(II) all exhibit paramagnetism at room temperature. Likewise, the rare earth metals Dy(III), Gd(III), and Nd(III) with eight coordinating species have also shown paramagnetism at ambient temperatures. Exposure to a magnetic field results in spin alignment of unpaired electrons in the 3d orbital for the transition metal MILs and the 4f orbital for rare earth MILs. Removal of the magnetic field results in random spin orientation due to thermal motion, which creates a loss of magnetization. Most paramagnetic materials exhibit an inverse relationship between magnetic susceptibility and temperature as defined by the Curie-Weiss law.

The $\mu_{eff}$ values for each exemplary MIL were determined using a Quantum Design MPMS SQUID magnetometer following procedures similar to those previously reported. (Y. Mudryk, P. Manfrinetti, V. Smetana, J. Liu, M. L. Fornasini, A. Provino, V. K. Pecharsky, G. J. Miller and K. A. Gschneidner, *J. Alloys Compd*, 2013, 557, 252-260).

FIG. 4a shows the temperature dependence of magnetization for the $[P_{66614}^+][Co(hfacac)_3^-]$ MIL. FIG. 4b shows a plot representing the linear portion of the reciprocal susceptibility versus temperature diagram for the octahedrally coordinated cobalt MIL. The calculated $\mu_{eff}$ for the $[P_{66614}^+][Co(hfacac)_3^-]$ MIL was $4.3\mu_B$, which agrees with previously reported literature values for high spin state Co(II) complexes.

Figure 5B:
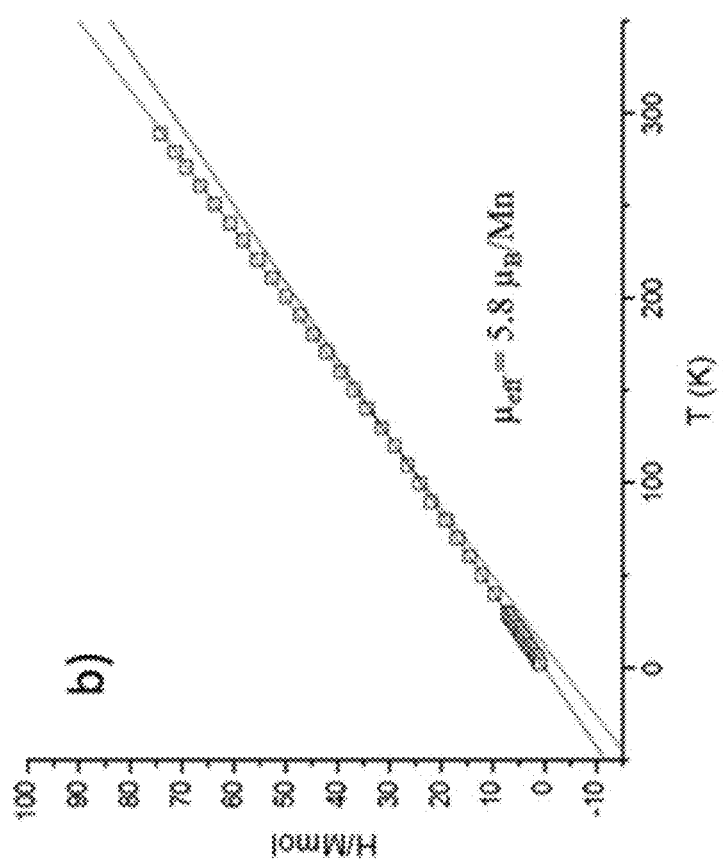
FIG. 5b shows the Curie-Weiss fits of both high- and low-temperature linear regions of the reciprocal susceptibility for the $[P_{66614}^+][Mn(hfacac)_3^-]$ MIL.
Figure 5A:
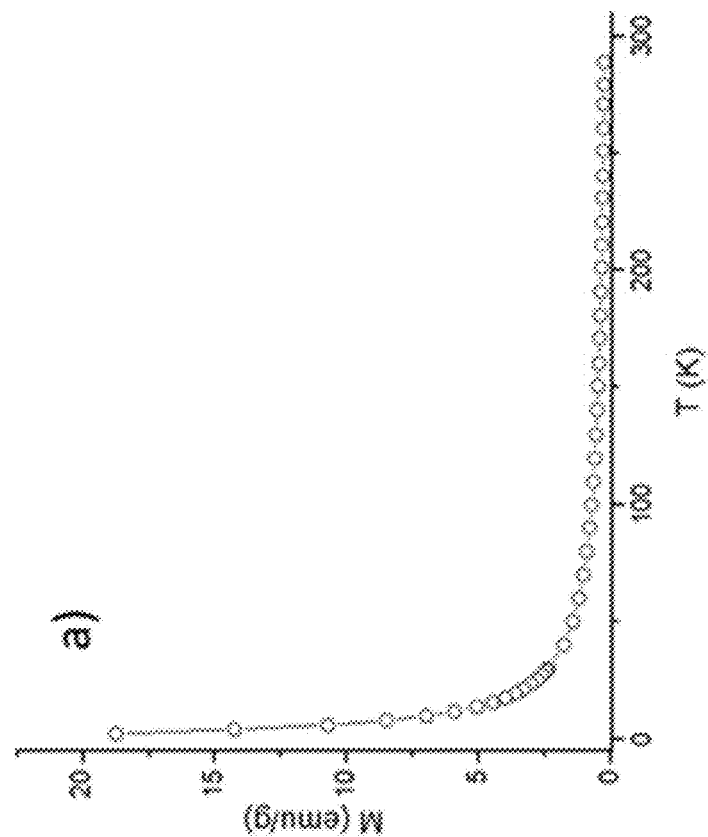
FIG. 5a shows the magnetization of the $[P_{66614}+][Mn(hfacac)_3^-]$ MIL measured as a function of temperature in a 20000 Oe applied magnetic field.

FIG. 5a shows magnetization of the $[P_{66614}^+][Mn(hfacac)_3^-]$ MIL measured as a function of temperature in a 20000 Oe applied magnetic field. FIG. 5b shows the Curie-Weiss fits of both high- and low-temperature linear regions of the reciprocal susceptibility for the $[P_{66614}^+][Mn(hfacac)_3^-]$ MIL. Therefore, the octahedrally coordinated $[P_{66614}^+][Mn(hfacac)_3^-]$ possesses a high-spin $d_5$ manganese(II) metal center and exhibits a $\mu_{eff}$ of $5.8\mu_B$ at lower temperatures which agrees with literature reports, but is slightly lower ($5.5\mu_B$) at higher temperatures.

FIG. 5a shows the magnetization of the $[P_{66614}^+][Ni(hfacac)_3^-]$ MIL measured as a function of temperature in a 20000 Oe applied magnetic field. FIG. 5b shows the Curie-Weiss fits of the linear regions of the reciprocal susceptibility above and below the ~150 K anomaly. Therefore, the nickel-based MIL exhibits a $\mu_{eff}$ of $2.8\mu_B$ at lower temperatures, also in agreement with literature values, but displays an anomaly in the temperature versus reciprocal mass susceptibility plot. This is presumably due to a phase transition of the MIL from a solid to liquid at approximately 150 K.

Figure 7B:
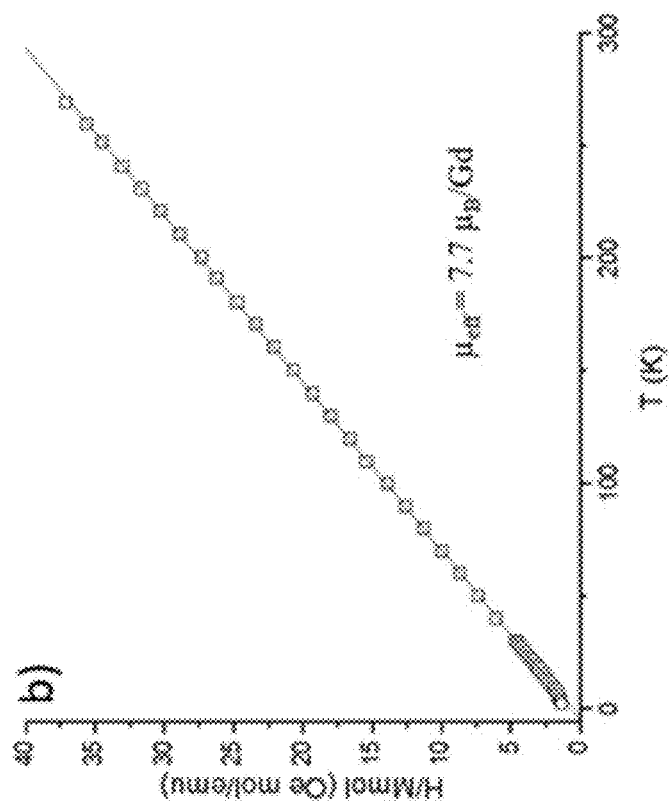
FIG. 7b shows the Curie-Weiss fit of the linear portion of the reciprocal susceptibility of the $[P_{66614}^+][Gd(hfacac)_4^-]$ MIL.
Figure 7A:
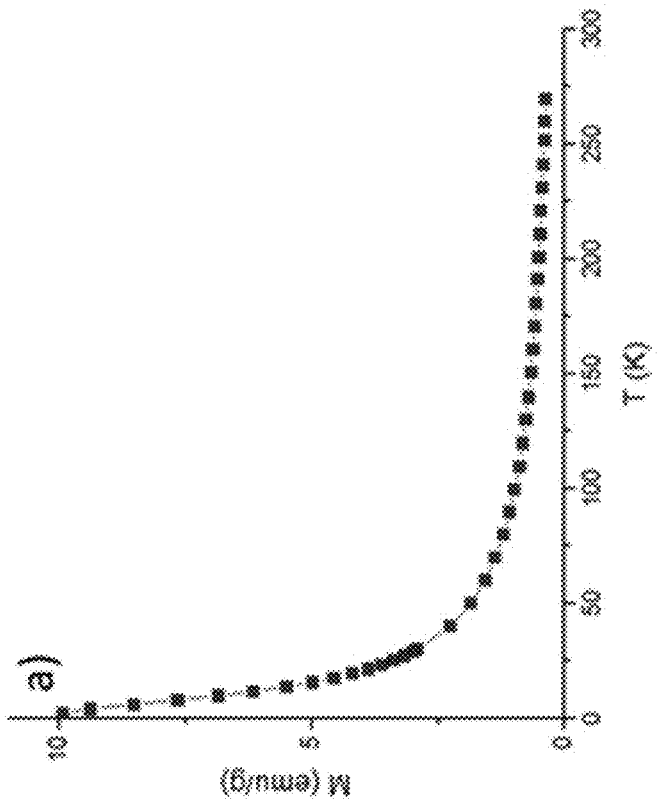
FIG. 7a shows Magnetization of the $[P_{66614}^+][Gd(hfacac)_4^-]$ MIL measured as a function of temperature in a 20000 Oe applied magnetic field.
Figure 8B:
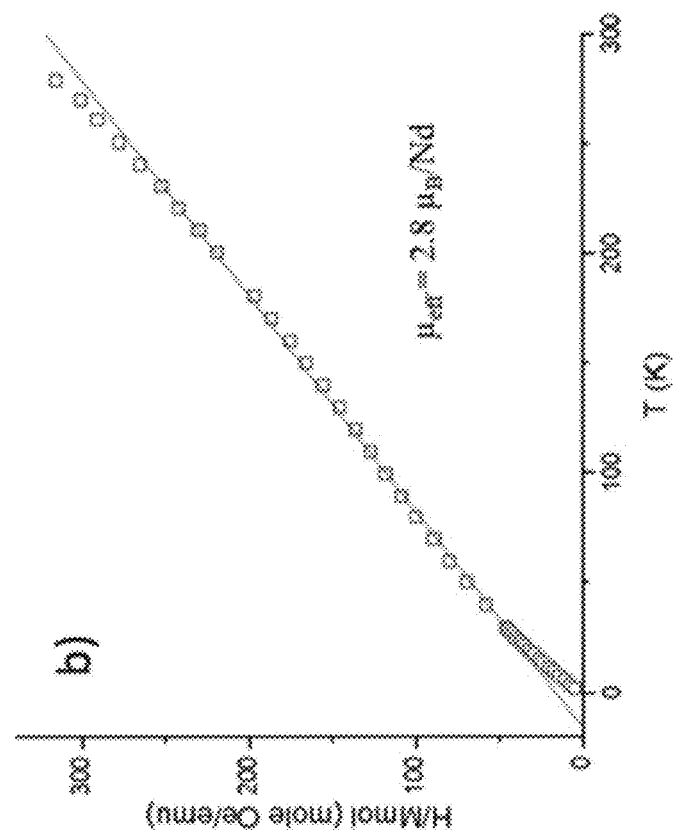
FIG. 8b shows the Curie-Weiss fit of the linear portion of the reciprocal susceptibility for the $[P_{66614}^+][Nd(hfacac)_4^-]$ MIL.
Figure 8A:
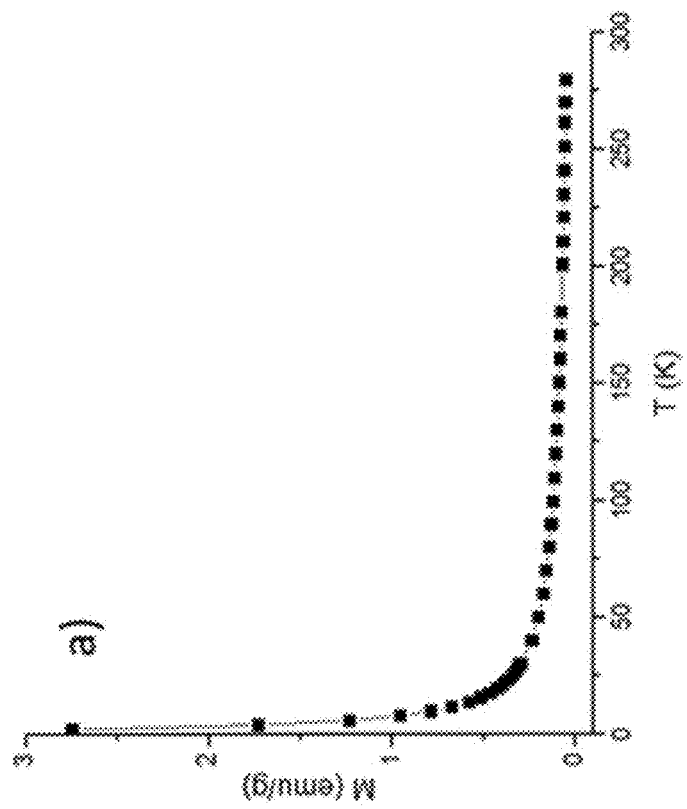
FIG. 8a shows the magnetization of the $[P_{66614}^+][Nd(hfacac)_4^-]$ MIL measured as a function of temperature in a 20000 Oe applied magnetic field.
Figure 9B:
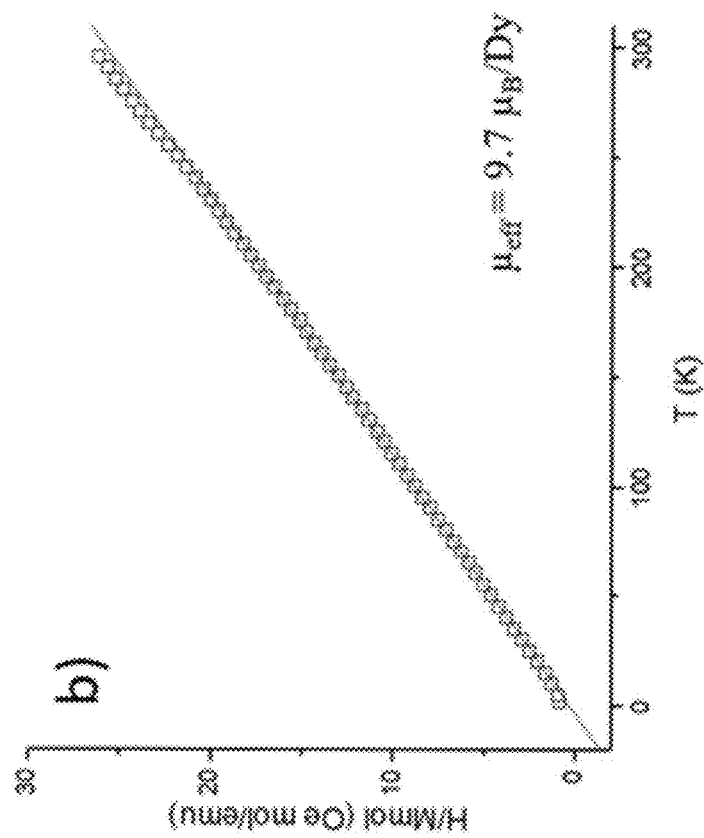
FIG. 9b shows the Curie-Weiss fit of the linear portion of the reciprocal susceptibility for the $[P_{66614}^+][Dy(hfacac)_4^-]$ MIL.
Figure 9A:
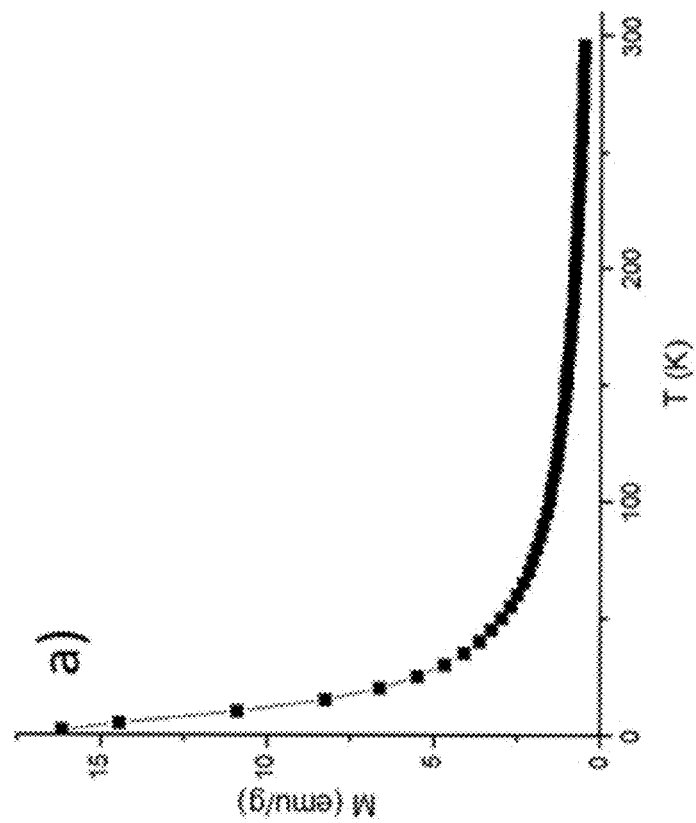
FIG. 9a shows the magnetization of the $[P_{66614}^+][Dy(hfacac)_4^-]$ MIL measured as a function of temperature in a 20000 Oe applied magnetic field.

MILs exhibiting higher magnetic susceptibility were achieved by chelating rare earth gadolinium(III) and dysprosium(III) ions possessing high magnetic moments into the anion structure. FIG. 7a, FIG. 8a, and FIG. 9a show the temperature dependence of magnetization for $[P_{66614}^+][Gd(hfacac)_4^-]$, $P_{66614}^+][Nd(hfacac)_4^-]$, and $[P_{66614}^+][Dy(hfacac)_4^-]$ MIL, respectively. FIG. 7a, FIG. 8a, and FIG. 9a show the plots of reciprocal susceptibility versus temperature for $[P_{66614}^+][Gd(hfacac)_4^-]$, $P_{66614}^+][Nd(hfacac)_4^-]$, and $[P_{66614}^+][Dy(hfacac)_4^-]$ MIL, and these plots show good linearity. The $\mu_{eff}$ of the dysprosium, gadolinium, and neodymium-based MILs were $9.7\mu_B$, $7.7\mu_B$, and $2.8\mu_B$, respectively, which are in accordance with previously reported eight coordinate dysprosium, gadolinium, and neodymium complexes. When collecting fine droplets of dispersed dysprosium and gadolinium based MILs, they can be observed to coalesce onto a rod magnet more easily compared to MILs with lower $\mu_{eff}$, including the neodymium and nickel-based MILs. However, all exemplary MILs synthesized in this disclosure respond sufficiently to a handheld rod magnet allowing for their removal from aqueous solution.

Example 4

Extraction of Viable *E. coli* Cells Using Hydrophobic MILs

The chemical structures of seven exemplary hydrophobic MILs that were used for the extraction of *E. coli* are shown in Table 2. To determine if MILs can extract viable *E. coli* cells, aqueous solutions of $1.68 \times 10^5$ CFUs $mL^{-1}$ were extracted with each of the seven MILs using an approach that is similar to one depicted in FIG. 10. Following back-extraction from the MIL phase with LB media and subsequent culture on selective agar plates, visible colonies were observed from the extractions employing the $[P_{66614}^+][Ni(hfacac)_3^-]$ and $[P_{66614}^+]$ $[Co(hfacac)_3^-]$ MILs with the greatest number of colonies obtained from the Ni(II)-based MIL extractions. These results indicated that the Ni(II) and Co(II)-based MILs were capable of extracting cells from aqueous solution and that the *E. coli* remained viable throughout the extraction and recovery process. Interestingly, the Mn(II) and rare earth-based MILs possess very similar chemical structures to the $[P_{66614}^+][Ni(hfacac)_3^-]$ and $[P_{66614}^+][Co(hfacac)_3^-]$ MILs, but did not yield any visible colonies when applied for cell extraction.

TABLE 2

Chemical Structures of the Seven Exemplary Magnetic Ionic Liquids Investigated for the Extraction of *E. coli* from Aqueous Samples

| No. | Cation | Anion | Viable Bacteria | Cytotoxicity to *E. coli* |
|---|---|---|---|---|
| 1 | $[P_{66614}^+]$ | $[FeCl_4^-]$ | No | Yes |

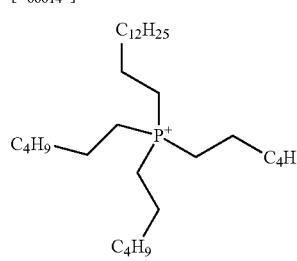

$([P_{66614}^+])$

TABLE 2-continued

Chemical Structures of the Seven Exemplary Magnetic Ionic Liquids
Investigated for the Extraction of E. coli from Aqueous Samples

| No. | Cation | Anion | Viable Bacteria | Cytotoxicity to E. coli |
|---|---|---|---|---|
| 2 | ([$P_{66614}^+$]) | [Co(hfacac)$_3^-$] | Yes | No |
| | | hfacac = $F_3C-C(O)-CH_2-C(O)-CF_3$ | | |
| 3 | ([$P_{66614}^+$]) | [Mn(hfacac)$_3^-$] | No | No |
| 4 | ([$P_{66614}^+$]) | [Ni(hfacac)$_3^-$] | Yes | No |
| 5 | ([$P_{66614}^+$]) | [Dy(hfacac)$_4^-$] | No | No |
| 6 | ([$P_{66614}^+$]) | [Gd(hfacac)$_4^-$] | No | Yes |
| 7 | ([$P_{66614}^+$]) | [Nd(hfacac)$_4^-$] | No | No |

Figure 11A:
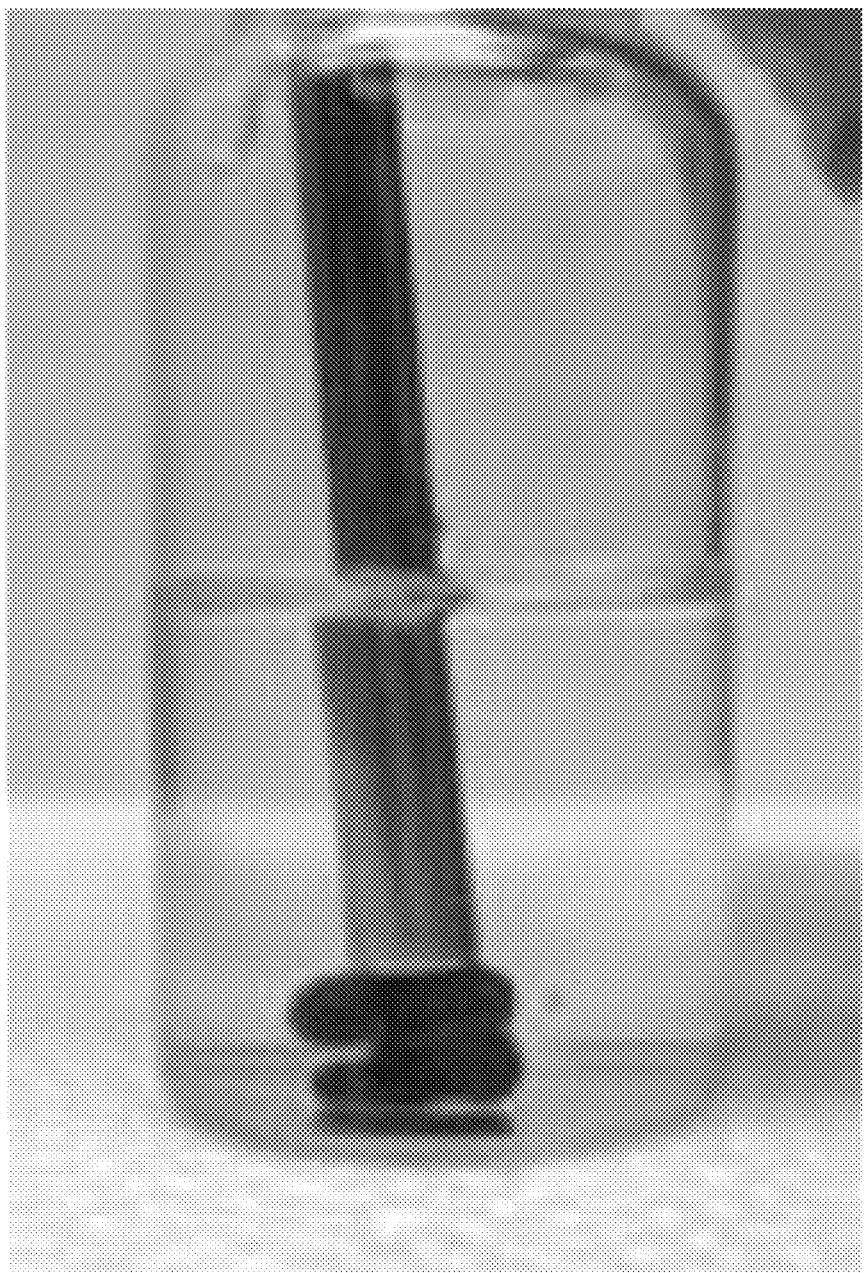
FIG. 11a and FIG. 11b show an exemplary procedure to separate the MIL from the sample.
Figure 11B:
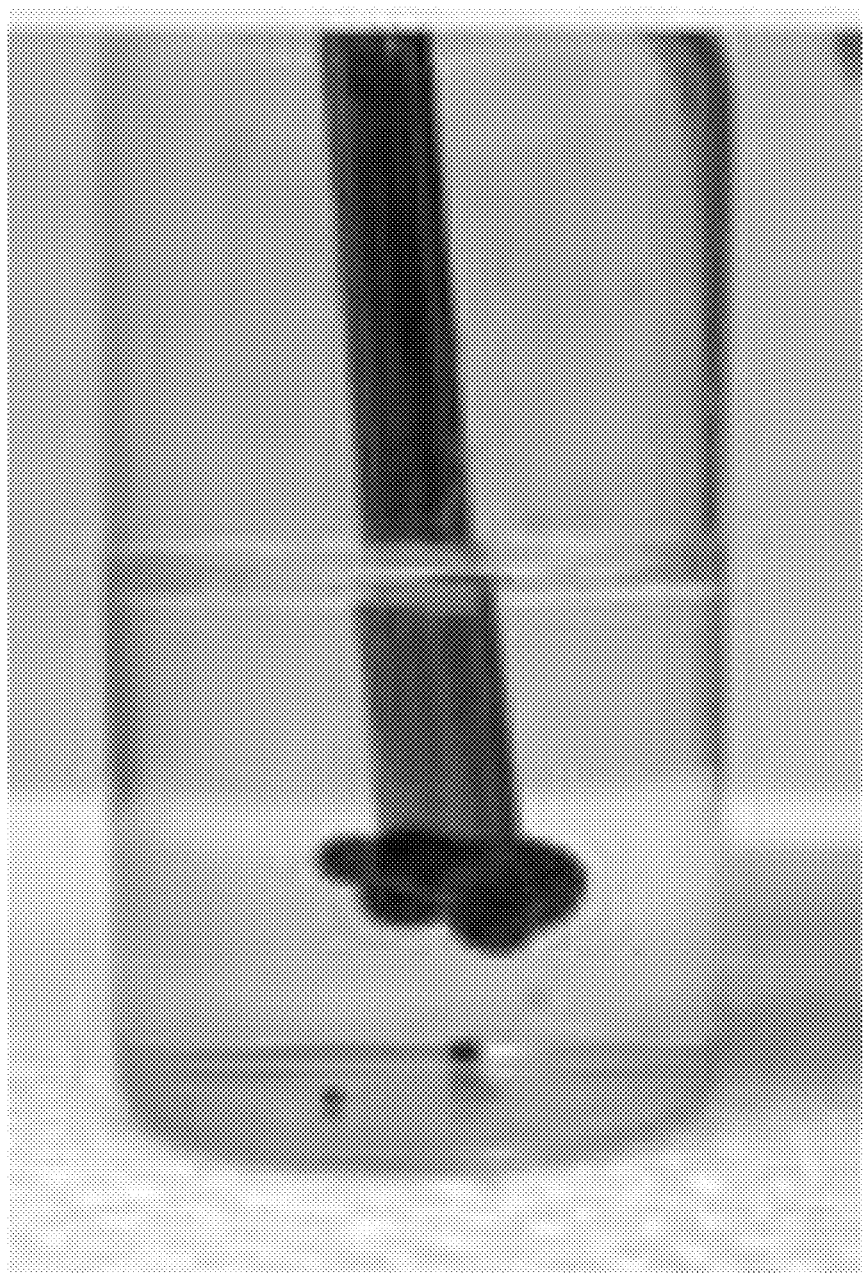

This example shows that a MIL-based method may provide a rapid approach for extracting and preconcentrating viable bacteria in which the extraction phase can be easily manipulated using a magnetic field. FIG. 11a and FIG. 11b show an exemplary procedure to separate a MIL from a sample. On contrast, the enrichment of viable bacteria from a sample solution is often accomplished using time-consuming culture-based methods that are tedious and difficult to automate. More importantly, this example shows that only some disclosed MILs herein can yield viable bacteria, while others and a similar prior art compound cannot.

Example 5

Cytotoxicity of MILs

Since culture-based methods are contingent upon the isolation of viable bacteria, the detection of *E. coli* following MIL-based cell extraction is influenced by the cytotoxicity of MILs. To study the effect of MILs on the growth of *E. coli*, a 1 mL aliquot of LB media was inoculated with $8.0 \times 10^2 \pm 0.5 \times 10^2$ CFUs mL$^{-1}$ and spiked with approximately 10 µL of a MIL. The mixture was agitated by vortex to simulate the recovery procedure after which a 100 µL aliquot of the suspension was plated on selective agar. When compared to a standard that had not been exposed to a MIL, the Ni(II), Co(II), Mn(II), Dy(III), and Nd(III)-based MILs had little to no influence on the growth of *E. coli*. However, the [$P_{66614}^+$][Gd(hfacac)$_4^-$] and [$P_{66614}^+$][FeCl$_4^-$] MILs hindered the proliferation of cells (as indicated by fewer observable colonies), suggesting that these MILs exhibit toxicity toward *E. coli* K12 cells. Although the mechanism for the decrease in cell viability is unknown, these findings are consistent with *E. coli* toxicity that was previously observed for Fe(III)-based MILs (Clark K D, Sorensen M, Nacham O, Anderson J L. Preservation of DNA in nuclease-rich samples using magnetic ionic liquids, *RSC Adv.* 2016; 6:39846-51).

Example 6

Figure 12:
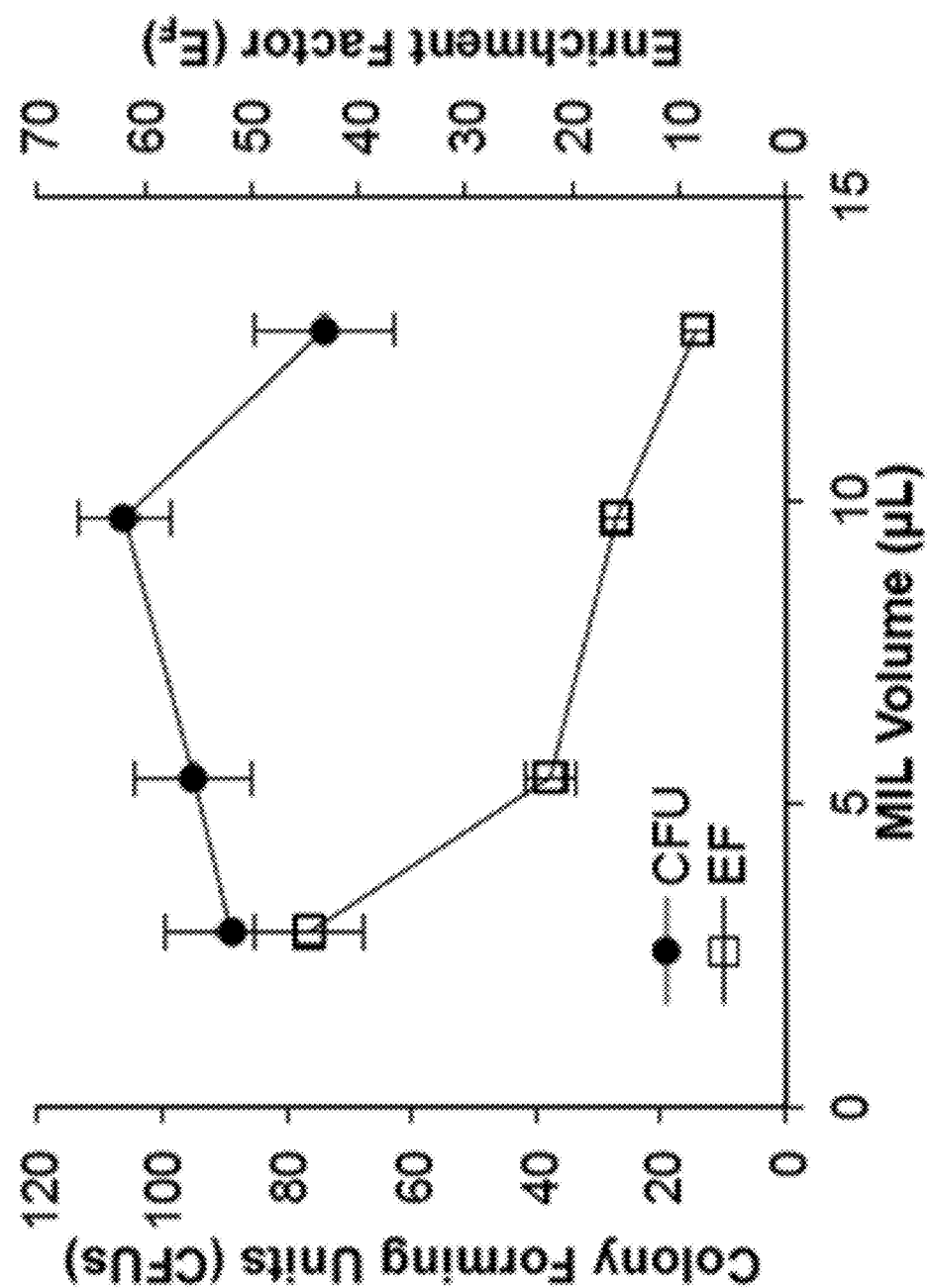
FIG. 12 shows the effect of MIL volume on the extraction of E. coli from aqueous solution.

Effect of MIL Volume on the Extraction and Preconcentration of *E. coli* from Aqueous Solution The effect of MIL volume on the extraction of *E. coli* was studied by varying the volume of [$P_{66614}^+$][Ni(hfacac)$_3^-$] added to an aqueous cell suspension at $1.68 \times 10^4$ CFUs mL$^{-1}$. Since $E_F$ values are highly dependent upon the volume of extraction phase, the exact volumes of MIL dispensed into the aqueous cell suspension were calculated from the mass of MIL added to the sample and MIL density. The calculated volumes were 2.89±0.24 µL, 5.42±0.15 µL, 9.72±0.38 µL, and 12.82±0.10 µL, corresponding to 5 µL, 10 µL, 15 µL, and 20 µL of MIL initially withdrawn into the pipette, respectively. Since the studied MILs exhibit remarkable hydrophobic character (as low as 0.01% (v/v)), their solubility in aqueous solution was negligible especially when considering the short duration of the extraction protocol. As shown in FIG. 12, an inverse relationship between MIL volume and $E_F$ was observed with a MIL volume of 5 µL resulting in the greatest $E_F$ value of 44.6±5.2. However, the total number of CFUs obtained following extraction remained consistent for the range of MIL volumes studied with relative standard deviations (RSD) from 7.0% to 12.5% (n=3). Since the lower MIL volumes tended to adhere to the walls of the sample vial and preclude manipulation of the extraction phase with a magnetic field, 9.72 µL of MIL (exact volume dispensed) was selected for subsequent experiments.

Example 7

Optimization of MIL-Based Cell Extraction

Figure 13:
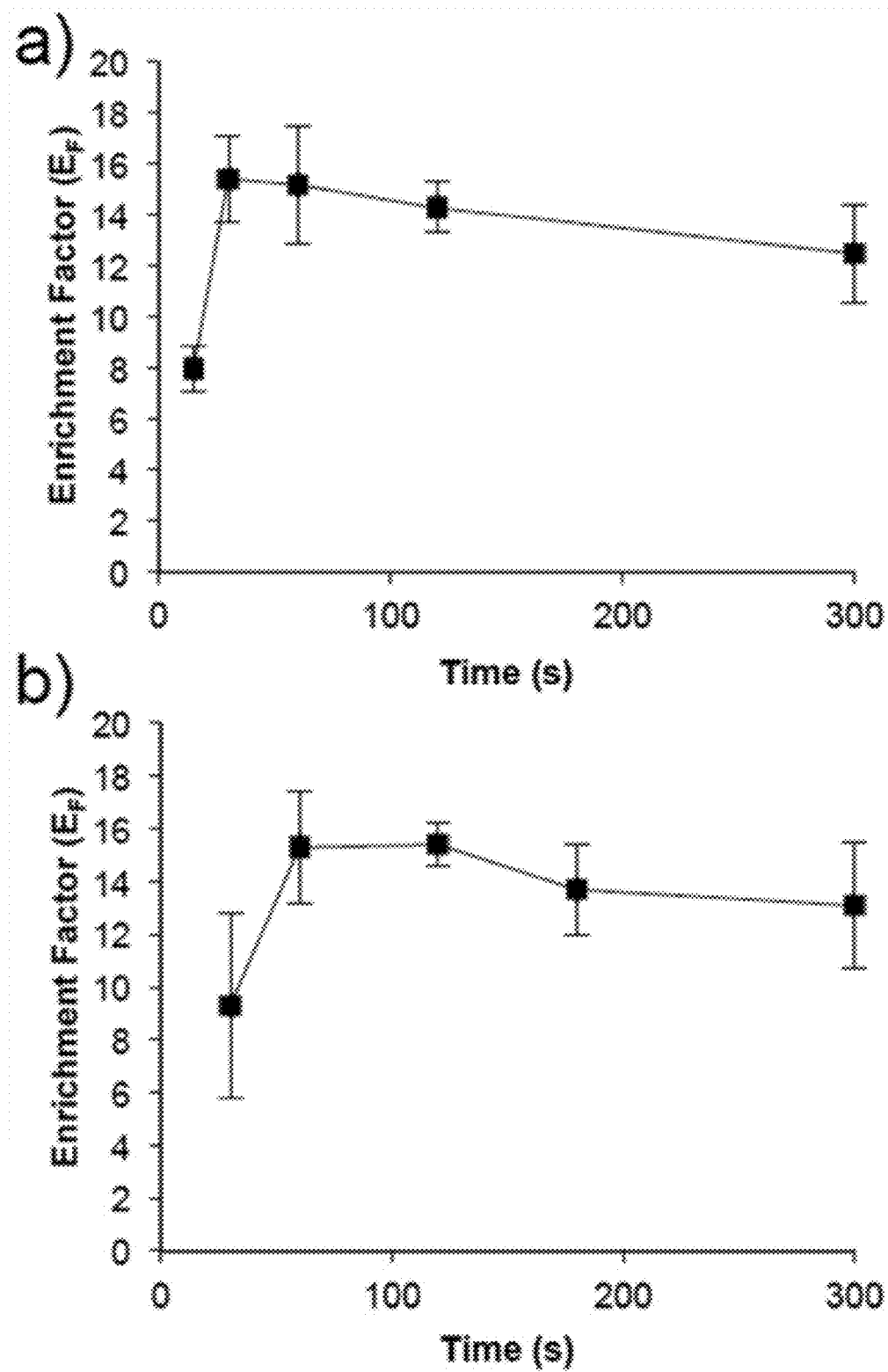
FIG. 13 shows the effect of a) extraction time and b) back extraction time on the preconcentration of E. coli from an aqueous solution.

The effect of extraction time on the enrichment of *E. coli* was investigated using the [$P_{66614}^+$][Ni(hfacac)$_3^-$] MIL from 15 s to 300 s. As shown in FIG. 13, an initial increase in $E_F$ was observed from 15 s to 30 s extraction after which the $E_F$ remained constant at approximately 15. The short duration required to achieve the maximum enrichment of viable *E. coli* is likely due to the dispersive nature of the extraction method where the formation of MIL microdroplets enables rapid mass transfer of cells from the aqueous sample to the MIL extraction phase. To maintain high $E_F$ values while minimizing the time required for extraction, an extraction time of 30 s was selected as optimal. The effect of back-extraction time on the recovery of viable cells from the MIL extraction phase was investigated using LB nutrient media from 30 s to 300 s. As shown in FIG. 13, the recovery of *E. coli* from the MIL was unchanged when back-extraction times longer than 60 s were applied. To ensure adequate mixing of the cell-enriched MIL with the back-extraction media, 120 s was selected for method yielding an $E_F$ of 15.4±0.8. Since the nutrient composition of growth media is also known to influence *E. coli* viability, the identity of the back-extraction solution was also studied. When the Mg$^{2+}$- rich SOC media was employed for cell recovery from the MIL (120 s back-extraction), no change in the $E_F$ was observed. Interestingly, deionized water and 10 mM Tris-HCl (pH 8) were tested as back-extraction solutions resulting in no detectable colonies after culture on the selective agar. Since the Gram negative *E. coli* possesses a negatively charged cell wall, this observation may be due to the high ionic strength of the nutrient media that assists in the recovery of the cells from the ionic extraction phase.

Example 8

Rapid Detection of *E. coli* with PCR Amplification

Figure 14:
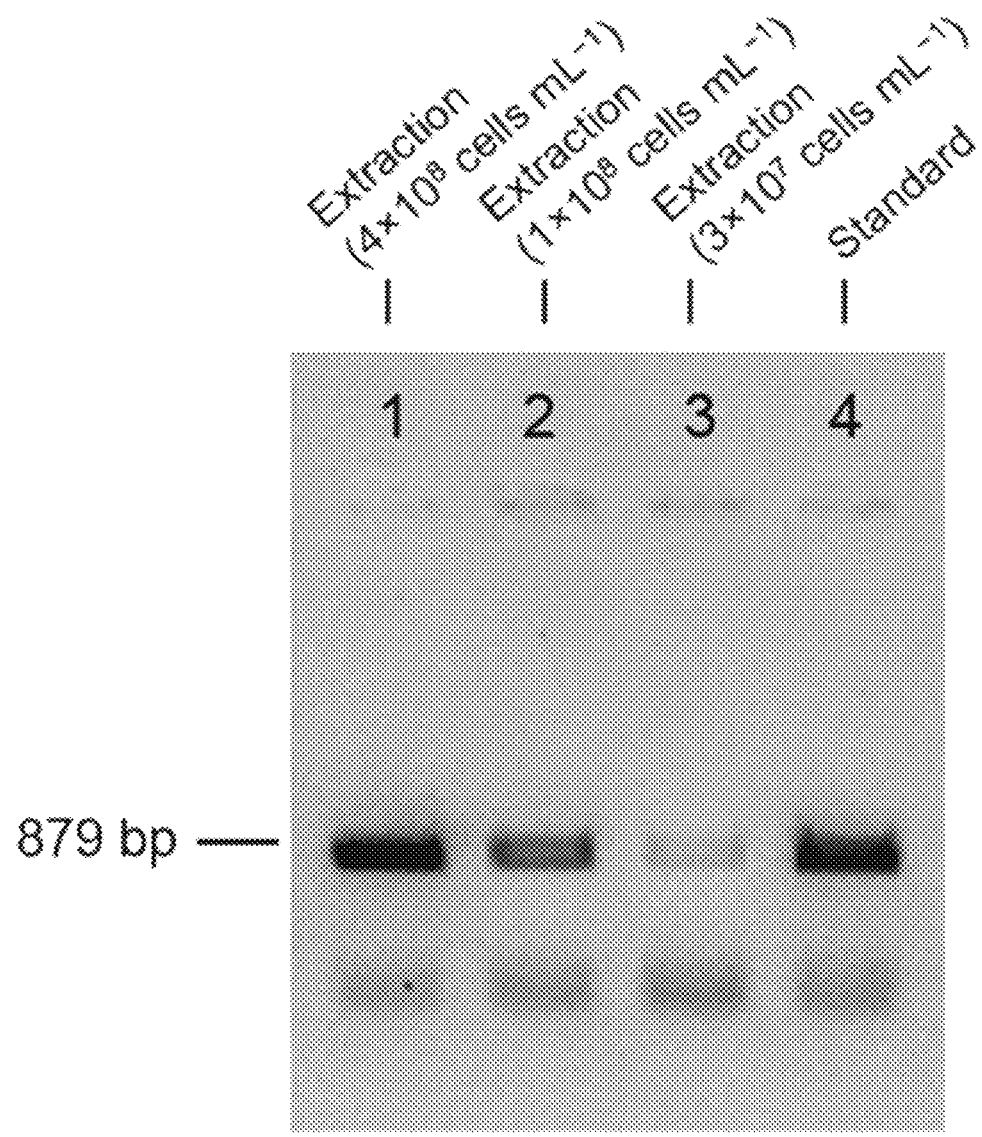
FIG. 14 shows an exemplary result of a direct PCR amplification of cell-enriched MIL following MIL-based extraction of whole E. coli cells.

Nucleic acid-based methods (e.g., PCR) have become increasingly popular for the detection of pathogens in food, environmental, and clinical samples to increase sample throughput and achieve lower detection limits. To demonstrate the compatibility of the MIL-based cell enrichment method with PCR amplification, aqueous samples were inoculated with *E. coli* transformants possessing the 879 bp MTAP gene at concentrations ranging from $4\times10^8$ to $3\times10^7$ CFUs $mL^{-1}$ and extracted using the $[P_{66614}^+][Co(hfacac)_3^-]$ MIL under optimized conditions. After extraction, 0.5 μL of the cell-enriched MIL phase was directly transferred into the PCR reagent mixture and heated at 95° C. for 5 min to induce cell lysis and the release of nucleic acids into solution. As shown in FIG. 14, decreasing intensity of the MTAP amplicon was observed as the concentration of cells in the sample solution was lowered. While the direct PCR detection modality provided a rapid assay for the detection of *E. coli*, the method was only suitable for the detection of relatively large quantities of cells (approximately $10^7$ CFUs $mL^{-1}$) in aqueous samples likely due to inhibition caused by the MIL.

Figure 15:
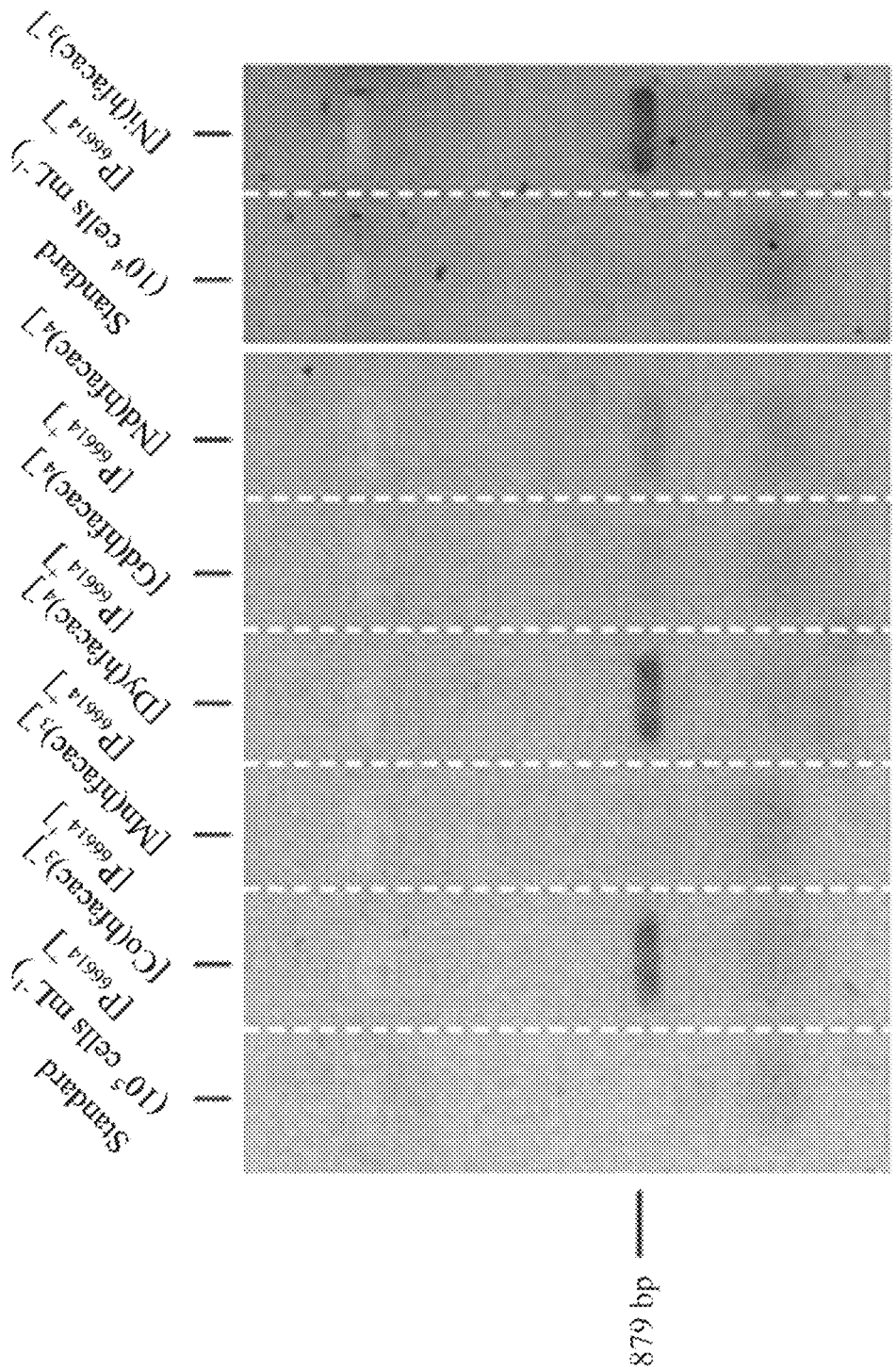
FIG. 15 shows an exemplary result of a PCR amplification following MIL-based extraction of whole E. coli cells.

To improve detection limits, cells were recovered from the MIL phase using nutrient broth and a 1 μL aliquot of LB media was analyzed by PCR amplification. The six hexafluoroacetylacetonate-based MILs were applied for the extraction of *E. coli* at concentrations as shown in FIG. 15, including the cell recovery step prior to PCR permitted the detection of bacterial pDNA from aqueous suspensions of *E. coli* at $1.68\times10^5$ CFUs $mL^{-1}$ when applying the $[P_{66614}^+][Co(hfacac)_3^-]$, $[P_{66614}^+][Dy(hfacac)_4^-]$, and $[P_{66614}^+][Nd(hfacac)_4^-]$ MILs as extraction media. However, the $[P_{66614}^+][Ni(hfacac)_3^-]$ MIL was the best performing extraction phase under the studied conditions providing sufficient cell enrichment for the detection of *E. coli* from a 2 mL sample containing $1.68\times10^4$ CFUs $mL^{-1}$. It is important to note that an aliquot of the aqueous cell suspension ($1.68\times10^5$ CFUs $mL^{-1}$) prior to MIL-based enrichment did not yield any detectable amplicon when subjected to PCR.

Since the $[Dy(hfacac)_4^-]$ and $[Nd(hfacac)_4^-]$-based MILs did not extract sufficient viable cells for culture-based detection, successful PCR amplification may have resulted from the extraction of cell-free DNA in the aqueous sample. To investigate this, 2 mL of an aqueous *E. coli* suspension ($1.68\times10^5$ CFUs $mL^{-1}$) were passed through a sterile 0.22 μm syringe filter and the filtrate (lacking *E. coli*) was extracted using the Dy(III) and Nd(III)-based MILs. No amplicon was detected following PCR, indicating that cell-free DNA was not extracted by the $[P_{66614}^+][Dy(hfacac)_4^-]$ and $[P_{66614}^+][Nd(hfacac)_4^-]$ MILs in sufficient quantity for detection by PCR. Similarly, no amplicon was detected after extracting the cell filtrate using the $[P_{66614}^+][Ni(hfacac)_3^-]$ MIL. These findings suggest that the PCR assay is more sensitive than the culture-based method following enrichment with the $[Dy(hfacac)_4^-]$ and $[Nd(hfacac)_4^-]$-based MILs, which is consistent with previous reports comparing the sensitivity of PCR and microbiological cultures for *E. coli* detection (Chapman P, Ellin M, Ashton R, Shafique W. Comparison of culture, PCR and immunoassays for detecting *Escherichia coli* 0157 following enrichment culture and immunomagnetic separation performed on naturally contaminated raw meat products, Int. J. Food Microbiol. 2001; 68:11-20 and Heininger A, Binder M. Schmidt S, Unertl K, Botzenhart K, Doring G, PCR and blood culture for detection of *Escherichia coli* bacteremia in rats, J. Clin. Microbiol. 1999; 37:2479-82). It should be noted that PCR assays are unable to distinguish between live and dead cells and, therefore, are complementary to microbiological culture for the determination of viable cells in a sample. The results demonstrate that MIL-based enrichment of bacteria is applicable for nucleic acid-based detection methods to provide increased sample throughput while simultaneously supporting culture-based assays for applications that require the identification of living microorganisms in a sample.

The invention is being thus described. It will be obvious that the same may be varied in many ways. Such variations are not to be regarded as a departure from the spirit and scope of the present disclosure and all such modifications are intended to be included within the scope of the following claims.

The above specification provides a description of various magnetic ionic liquids, methods of synthesizing and using the magnetic ionic liquids to extract a viable bacterium. Since many embodiments can be made without departing from the spirit and scope of the present disclosure, the invention resides in the claims.

What is claimed is:

1. A magnetic ionic liquid, comprising
a paramagnetic anionic component and a cationic component,
wherein the cationic component has a general formula (I)

wherein each of the $R^1$, $R^2$, $R^3$, and $R^4$ is independently a $C_2$-$C_{20}$ unsubstituted alkyl, and at least two of $R^1$, $R^2$, $R^3$, and $R^4$ are the same;
the paramagnetic anionic component has the following general formula (II),

wherein M is Co, Mn, Ni, Dy, Nd, Gd ion or a combination thereof; and
Y is a chelating agent having the general formula (III),

each of the $R^{10}$ and $R^{11}$ are independently a $CH_3$, $CHF_2$, $CH_2F$, or $CF_3$ group; and x is 3 or 4.

2. A magnetic ionic liquid, comprising
a paramagnetic anionic component and a cationic component,
wherein the cationic component has a general formula (I)

wherein each of the $R^1$, $R^2$, $R^3$, and $R^4$ is independently a $C_2$-$C_{20}$ unsubstituted alkyl, and at least two of $R^1$, $R^2$, $R^3$, and $R^4$ are the same;

the paramagnetic anionic component is [Co(hfacac)₃⁻], [Ni(hfacac)₃⁻], ([Mn(hfacac)₃⁻]), ([Dy(hfacac)₄⁻]), ([Gd(hfacac)₄⁻]), ([Nd(hfacac)₄⁻]), or combination thereof, wherein hfacac is

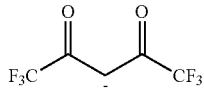

wherein each of the $R^{10}$ and $R^{11}$ are independently a substituted or unsubstituted methyl, phenyl, thiophenyl, napthyl, alkyl, or aryl group; and x is 3 or 4.

3. The magnetic ionic liquid of claim 1, wherein for the cationic component, at least one of $R^1$-$R^4$ group is different from the others.

4. The magnetic ionic liquid of claim 1, wherein the cationic component is $[(PR^1R^2R^3R^4)^+]$, wherein each of the $R^1$, $R^2$, and $R^3$ is independently a $C_6$ alkyl, and $R^4$ is a $C_{14}$ alkyl.

5. The magnetic ionic liquid of claim 1, wherein the magnetic ionic liquid is water insoluble.

6. The magnetic ionic liquid of claim 1, wherein the magnetic ionic liquid has a viscosity of from about 150 cp to about 1,000 cp at the temperature of 23.7° C.

7. The magnetic ionic liquid of claim 1, wherein the magnetic ionic liquid has a magnetic susceptibility of from about $2.5\mu_B$ to about $10.0\mu_B$, measured by a SQUID magnetometer.

8. The magnetic ionic liquid of claim 1, wherein the magnetic ionic liquid is soluble in hexane, heptane, toluene, and benzene at 10% (v/v) MIL to solvent ratio, in acetone, acetonitrile, chloroform, dichloromethane, dioxane, ethanol, ethyl acetate, diethyl ether, methanol, or isopropyl alcohol at 20% (v/v) MIL to solvent ratio, or in hexane, heptane, toluene, and benzene at 20% (v/v) MIL to solvent ratio.

9. The magnetic ionic liquid of claim 1, wherein the magnetic ionic liquid keeps a bacterium viable.

10. A method of extracting, detecting, identifying, quantifying, or a combination thereof a viable bacterium from a sample, comprising:
    contacting a sample with a magnetic ionic liquid of claim 1 for the period of a contacting time,
    wherein the sample comprises a viable bacterium; and the magnetic ionic liquid extracts the bacterium from the sample.

11. The method of claim 10, wherein the method further comprises detecting the bacteria by a culture-based or nucleic acid-based method for pathogen detection.

12. The method of claim 10, wherein the bacterium is a Gram-negative bacterium, *E. coli*, Gram positive bacterium, *M. smegmatis*, or a combination thereof.

13. The method of claim 10, wherein the sample is a heterogeneous aqueous solution comprising food, milk, juices, biological fluid, blood, environmental water or soil, or any suspended solid.

14. The method of claim 11, wherein the detecting comprises using a nucleic acid-based method.

15. The method of claim 11, wherein the detecting comprises using PCR amplification in a PCR reagent mixture for a gene or genes in the bacterium.

16. The method of claim 11, wherein the detecting comprises using reverse transcription PCR (RT-PCR) for mRNA in the bacterium.

17. The method of claim 11, wherein the detecting comprises using mass/flow cytometry.

18. The method of claim 11, wherein the detecting comprises using a culture-based method.

19. The method of claim 10, wherein the method further comprises back-extracting the bacterium from the magnetic ionic liquid to a back extraction solution.

20. The method of claim 19, wherein the back extraction solution is a nutrient broth, salt solution, or aqueous medium that recovers the bacteria from the MIL.

21. The method of claim 10, wherein the contacting time is from about 30 second to about 10 min.

22. The method of claim 10, wherein the method further comprises separating the magnetic ionic liquid from the sample by a magnetic field.

23. The method of claim 10, wherein the method further comprises separating the magnetic ionic liquid from the sample by a magnetic field of from about 0.1 tesla to about 2 tesla.

24. The method of claim 10, wherein the bacterium is viable in the MTh.

25. The magnetic ionic liquid of claim 2, wherein for the cationic component, at least one of $R^1$-$R^4$ group is different from the others.

26. The magnetic ionic liquid of claim 2, wherein the cationic component is $[(PR^1R^2R^3R^4)^+]$, wherein each of the $R^1$, $R^2$, and $R^3$ is independently a $C_6$ alkyl, and $R^4$ is a $C_{14}$ alkyl.

27. The magnetic ionic liquid of claim 2, wherein the magnetic ionic liquid is water insoluble.

28. The magnetic ionic liquid of claim 2, wherein the magnetic ionic liquid has a viscosity of from about 150 cp to about 1,000 cp at the temperature of 23.7° C.

29. The magnetic ionic liquid of claim 2, wherein the magnetic ionic liquid has a magnetic susceptibility of from about $2.5\mu_B$ to about $10.0\mu_B$, measured by a SQUID magnetometer.

30. The magnetic ionic liquid of claim 2, wherein the magnetic ionic liquid is soluble in hexane, heptane, toluene, and benzene at 10% (v/v) MIL to solvent ratio, in acetone, acetonitrile, chloroform, dichloromethane, dioxane, ethanol, ethyl acetate, diethyl ether, methanol, or isopropyl alcohol at 20% (v/v) MTh to solvent ratio, or in hexane, heptane, toluene, and benzene at 20% (v/v) MTh to solvent ratio.

31. The magnetic ionic liquid of claim 2, wherein the magnetic ionic liquid keeps a bacterium viable.

* * * * *